(12) United States Patent
Sakata et al.

(10) Patent No.: US 7,416,326 B2
(45) Date of Patent: Aug. 26, 2008

(54) APPARATUS FOR PRODUCING STERILIZED WATER

(75) Inventors: Yu Sakata, Yokohama (JP); Toshio Okazaki, Kamifukuoka (JP); Toshizumi Ikeda, Fujimi (JP)

(73) Assignee: Family-Life Co., Ltd., Tokyo (JP)

( * ) Notice: Subject to any disclaimer, the term of this patent is extended or adjusted under 35 U.S.C. 154(b) by 322 days.

(21) Appl. No.: 10/512,909

(22) PCT Filed: May 8, 2003

(86) PCT No.: PCT/JP03/05767

§ 371 (c)(1),
(2), (4) Date: Oct. 29, 2004

(87) PCT Pub. No.: WO03/094980

PCT Pub. Date: Nov. 20, 2003

(65) Prior Publication Data

US 2005/0218054 A1    Oct. 6, 2005

(30) Foreign Application Priority Data

May 10, 2002  (JP)  ............ 2002-134785
Nov. 1, 2002  (JP)  ............ 2002-319214
Dec. 26, 2002  (JP)  ............ 2002-376382

(51) Int. Cl.
*B01F 5/04*  (2006.01)
*B01F 5/06*  (2006.01)

(52) U.S. Cl. ............ 366/163.2; 366/181.5; 366/337; 137/889

(58) Field of Classification Search ............ 366/163.1, 366/163.2, 167.1, 173.1, 176.1, 174.1, 337, 366/175.2, 181.5, 181.8, 182.4, 182.2; 137/889, 137/892–896
See application file for complete search history.

(56) References Cited

U.S. PATENT DOCUMENTS 3,643,688 A * 2/1972 Meinert (Continued)

FOREIGN PATENT DOCUMENTS

EP    889244 A2 *  1/1999

(Continued)

OTHER PUBLICATIONS

International Search Report for PCT/JP 03/05767. dated Aug. 2003.

(Continued)

*Primary Examiner*—Charles E Cooley
(74) *Attorney, Agent, or Firm*—Myers Bigel Sibley & Sajovec

(57) ABSTRACT

There is provided an apparatus for manufacturing sterilizing water, in which the sterilization power of a chlorine-based solution consisting of sodium hypochlorite or chlorine dioxide or a mixture thereof is fully achieved while the generation of chlorine gas is restrained, and desired sterilizing water is manufactured by properly feeding and mixing three liquids of water, an acid solution, and a chlorine-based solution at a fully controlled concentration. In the apparatus for manufacturing sterilizing water of some aspect of the present invention, after both acid solution and chlorine-based solution have been diluted with raw water in a feeder, the dilute solutions can be mixed with each other by a mixer.

11 Claims, 17 Drawing Sheets

U.S. PATENT DOCUMENTS

| | | | |
|---|---|---|---|
| 4,265,275 A * | 5/1981 | Heller et al. | |
| 4,352,378 A * | 10/1982 | Bergmann et al. | 366/337 |
| 4,416,610 A * | 11/1983 | Gallagher, Jr. | 137/889 |
| 4,441,823 A * | 4/1984 | Power | 366/167.1 |
| 4,673,335 A * | 6/1987 | Nicodemus | |
| 5,427,151 A * | 6/1995 | Pauley | 137/895 |
| 5,865,537 A * | 2/1999 | Streiff et al. | 366/174.1 |
| 6,293,294 B1 * | 9/2001 | Loeb et al. | 137/889 |
| 6,293,394 B1 * | 9/2001 | Marbler et al. | |
| 6,523,991 B1 * | 2/2003 | Maklad | 366/163.2 |
| 6,969,052 B2 * | 11/2005 | Korzeniowski | 366/163.2 |

FOREIGN PATENT DOCUMENTS

| | | | |
|---|---|---|---|
| JP | 53-31255 | | 3/1978 |
| JP | 54-123775 | | 9/1979 |
| JP | 04-135633 | | 5/1992 |
| JP | 10-141299 | * | 5/1998 |
| JP | 10-182325 | | 7/1998 |
| JP | 11-188083 | | 7/1999 |
| JP | 01-321778 | | 11/2001 |
| JP | 2001-321778 | | 11/2001 |
| JP | 2002-316169 | | 10/2002 |
| JP | 2003-200174 | | 7/2003 |
| WO | 96/10541 | | 4/1996 |

OTHER PUBLICATIONS

Japanese Official Action for Patent Application No. 2002-134785, mailed Mar. 11, 2008.

Partial Translation of Japanese Official Action for Patent Application No. 2002-134785, mailed Mar. 11, 2008.

* cited by examiner

FIG.5
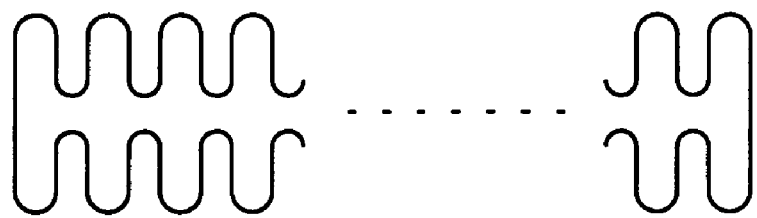
(A)
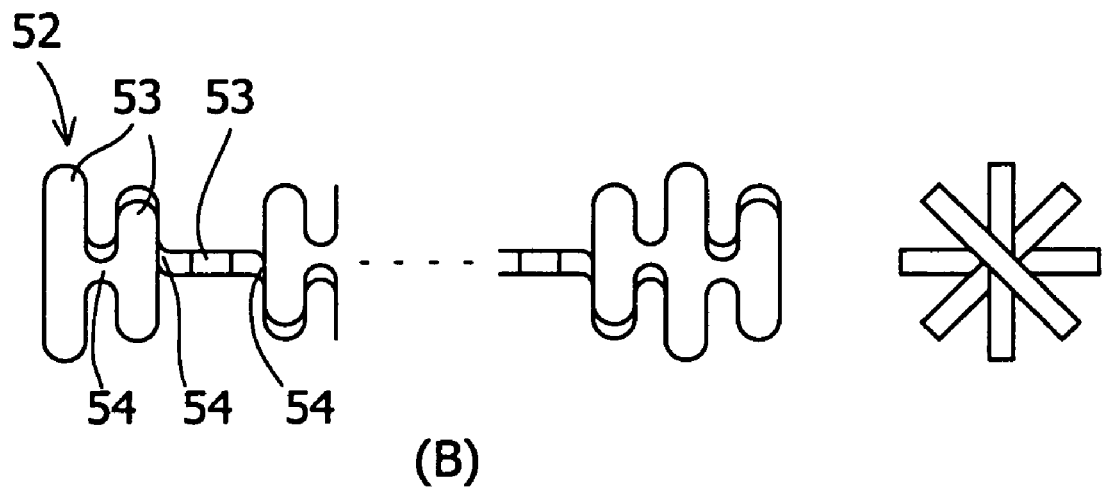
(B)
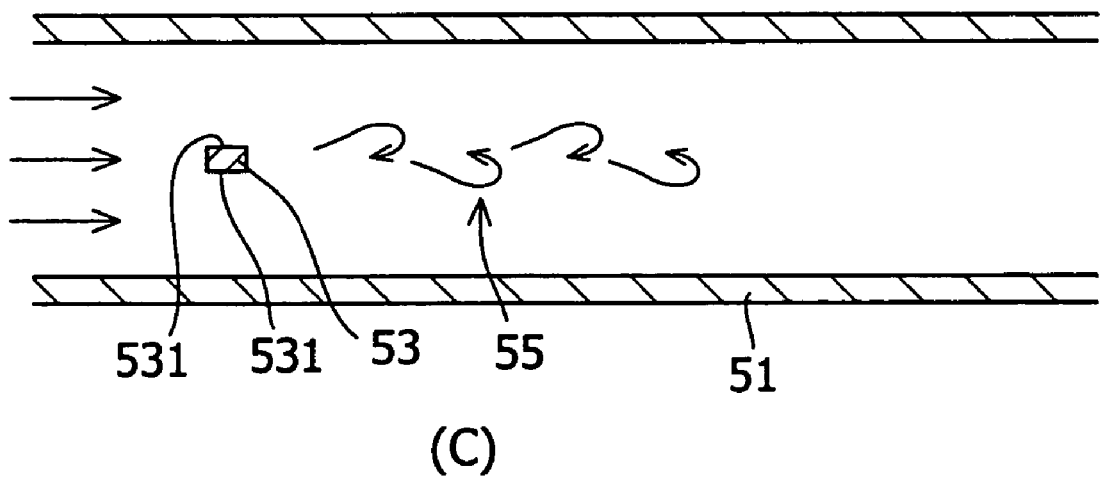
(C)

APPARATUS FOR PRODUCING STERILIZED WATER

RELATED APPLICATIONS

The present application is a National Phase application of PCT/JP03/05767 filed on May 8, 2003, which claims priority from Japanese Patent Application Numbers 2002-134785 filed May 10, 2002; 2002-319214 filed Nov. 1, 2002; and 2002-376382 filed Dec. 26, 2002, the disclosures of which are incorporated herein by reference.

FIELD OF THE INVENTION

The present invention relates to an apparatus for manufacturing sterilizing water used for food processing, stock raising, medical care, and the like. More particularly, it relates to an apparatus for manufacturing sterilizing water that accomplishes chlorination by sodium hypochlorite solution or chlorine dioxide solution.

BACKGROUND OF THE INVENTION

Conventionally, sodium hypochlorite solution having sterilizing properties has been used as a bleaching agent or a mold remover. Also, the use of chlorine dioxide for sterilization of city water has been studied. Such sterilizing water in which the concentration of chlorine is increased as compared with city water etc. to enhance the sterilization power has been used at job sites requiring sterilization, for example, for HACCP-compatible food processing, stock raising such as breeding of SPF pigs, and medical care.

It is known that the bactericidal action of the above-described chlorine-based compound changes greatly according to the state of the chlorine-based compound in aqueous solution, and depends heavily on the acidity (pH). Especially in the case of sodium hypochlorite, bactericidal action differs greatly depending on the pH range, between a strongly acidic condition, a weakly acidic through neutral condition, and an alkaline condition.

In the strongly acidic condition (where pH is lower than 3.8), chlorine gas is liberated from sodium hypochlorite solution. This chlorine gas is toxic, and hence the application of the manufactured sterilizing water is undesirably limited to a substantial extent, though the sterilizing water has a bactericidal action. Also, in the alkaline condition (where pH exceeds 7.5), the ratio of ionization of chlorine in the solution into the form of hypochlorous acid ion (OCl—) increases. The hypochlorous acid ion has weak sterilization power, being about 1/80 of the sterilization power of hypochlorous acid (HOCl) with the same chlorine concentration. Therefore, to raise the sterilization power, the chlorine concentration must inevitably be increased. However, even if sterilization power is raised by increasing the concentration, though sterilization power rises, the concentration has to be increased still further, since sodium hypochlorite solution itself is alkaline.

On the other hand, in the weakly acidic through neutral condition (where pH is in the range of 4.8 to 7.5), a large amount of chlorine takes the form of hypochlorous acid (HOCl), so that the sterilization power can desirably be raised without the production of chlorine gas. For example, Japanese Patent Provisional Publication No. 10-182325 (No. 182325/1998) has discloses a "Device for Reinforcing Sterilization Power of Sodium Hypochlorite". This Document discloses that either acid or chlorine-based solution is diluted and fed to a water flow by separate feeders. In this disclosure, acid solution or chlorine-based solution is poured into a flow path by a pump. A configuration is mainly disclosed, in which hypochlorous acid is fed to the water flow from a chlorine-based solution tank by a pump, and subsequently acid is fed by a pump. Further, in mixing, mixing means consisting of an agitator or the like is used.

However, the apparatus and method for manufacturing sterilizing water disclosed until now have the following problems:

(1) In the publicly known configuration, an acid is used to make the liquid into a weakly acidic condition, wherein the finally manufactured sterilizing water, chlorine gas is liable to be produced due to nonuniform concentration of acid or hypochlorous acid.

(2) In order to control the acidic water to which sodium hypochlorite solution is fed so as to provide a proper acidity, a precise control system is needed, and also, a plurality of feeders are needed. Thus, the apparatus becomes large in scale, and the installation location is limited, resulting in a high cost.

(3) Also, a pump is used to feed acid or sodium hypochlorite, meaning that the pump must be controlled with high accuracy.

Furthermore, while an agitator etc. could also be used in a mixer, such a configuration has the following problems:

(4) A mixer which comprises an agitator or the like desirably has a fixed shape in order to mix the liquid efficiently, but the material thereof is limited because the mixer itself is used to mix solutions in a wide range of acidity conditions, from acidic condition to alkaline condition. In particular, when a resin is used to make a mixer, no suitable mixer is known in terms of acid resistance and alkali resistance.

(5) Where the flow path must be straight in order to arrange the mixer in the flow path, the design of the whole of the apparatus is severely restricted, and making the equipment smaller is hindered.

Furthermore, a Venturi type feeding method, which utilizes negative pressure, could also be adopted for feeding acid or hypochlorous acid according to the quantity of production per unit time of the sterilizing water. However, this method has the following problems:

(6) Where a pump for producing a water flow is arranged on the upstream side of a mixer, acidic water is produced by a Venturi type feeder and further sodium hypochlorite solution is fed by the Venturi type feeder, and a faucet etc. are provided on the downstream side thereof as an outlet for the sterilizing water. In such a case, since the degree of opening of the faucet can be adjusted arbitrarily, acid solution and sodium hypochlorite solution must be fed in proportion to the current flow rate according to the degree of opening of the faucet.

(7) With this method, it is necessary to precisely control a very low flow rate of the feed chemical. If the flow rate is controlled by using a needle type flow regulator, the shape of an opening for restricting the flow rate becomes a doughnut shape or the like having a very small cross section, so that the flow rate is varied by the deformation of flow regulator due to thermal expansion of material of the flow regulator caused by a change in environmental temperature. This phenomenon is particularly prominent when the flow regulator is made of a resin to ensure chemical resistance. Further, if small quantities of dust etc. are contained in the flowing liquid, the flow path is soon clogged, which hinders stable feeding operation.

(8) The negative pressure for this suction feeding operation is approximately 100 to 1000 mm in water-gauge pressure (=about 980 to 9800 Pa=about 0.00968 to 0.0968 atm). This negative pressure is at the same level as the pressure produced by a difference in height of water of about 10 cm. Therefore, the flow rate of the suction fed liquid is affected by a minute change in pressure of water flow that achieves suction.

(9) When the whole of the apparatus is in actual use, it is favorable to provide a safety device that monitors the quantity of feeding of acid or hypochlorous acid as appropriate so that the supply of sterilizing water is shut off when the flow rate exceeds a certain value. In this case, the manufacture path of sterilizing water can be shut off by using an electromagnetic valve etc. as the safety device. However, if the flow rate in the supply path of acid or hypochlorous acid is used as the judgment criterion, a flow sensor is needed to detect the flow rate in the supply path of acid or hypochlorous acid. An inexpensive flow sensor that has high chemical resistance and is capable of detecting a very low flow rate sensitively is not yet known.

(10) Furthermore, if the path to be detected contains air bubbles, the flow sensor generally produces an error. When the apparatus for manufacturing sterilizing water is in actual use, it is favorable to maintain a state in which air bubbles do not intrude into the path during the operation and shutdown of the apparatus.

(11) Also, when acidic solution or chlorine-based solution is fed at a low flow rate, even if it is attempted to directly regulate the quantity of feeding thereof, dust etc. contained in the solution exerts an influence on the regulating portion, so that it is not easy to perform stable operation for a long period of time.

SUMMARY OF THE INVENTION

The present invention has been made to solve at least some of the above-described problems. An object of the present invention is to provide an apparatus for manufacturing sterilizing water, which fully achieves the sterilization power of a chlorine-based solution while restraining the generation of chlorine gas, and has a simple construction. Another object of the present invention is to provide an apparatus for manufacturing sterilizing water, which restrains fluctuations of pressure affecting feeding, and thereby realizing stable. feeding. Still another object of the present invention is to provide a mixer capable of accomplishing mixing properly at a low cost, a flow rate regulator capable of stably restricting the flow rate even if the flow rate is very low, and an inexpensive flow sensor capable of detecting a very low flow rate properly.

In the present invention, there is provided an apparatus for manufacturing sterilizing water, which can manufacture desired sterilizing water by properly feeding and mixing three liquids of water, an acid solution, and a chlorine-based solution at a fully controlled concentration. The water is used in larger quantities than the acid solution and chlorine-based solution. In the apparatus for manufacturing sterilizing water in accordance with the present invention, after both of the acid solution and the chlorine-based solution have been diluted with raw water in a feeder, the dilute solutions can be mixed with each other.

Therefore, the present invention provides an apparatus for manufacturing sterilizing water, in which sterilizing water is manufactured by mixing an acid solution consisting of hydrochloric acid or acetic acid or a mixture thereof and a chlorine-based solution consisting of sodium hypochlorite or chlorine dioxide or a mixture thereof with water, including a feeder provided with a first flow path, in which the acid solution is fed to a part of a water flow to produce a dilute acid solution, and a second flow path, in which the chlorine-based solution is fed to the remainder of the water flow to produce a dilute chlorine-based solution; and a mixer which is arranged on the downstream side of the first and second flow paths to mix the dilute acid solution sent from the first flow path with the dilute chlorine-based solution sent from the second flow path.

By this configuration, the acid solution and chlorine-based solution can be fed and mixed while being diluted without the use of a plurality of feeders, so that an apparatus for manufacturing sterilizing water having a simple construction can be manufactured.

In this configuration, the configuration can be made such that the feeder is a feeder for feeding the acid solution and the chlorine-based solution by suction utilizing a negative pressure produced in water flows in the first and second flow paths, so that feeding using a pump is not performed.

A line pump is not needed in the feeding lines for the acid solution and the chlorine-based solution, so that the apparatus for manufacturing easily.

Further, in the above-described apparatus for manufacturing sterilizing water, the configuration can be made such that the first and second flow paths are separated by a separation wall.

The separation wall has a function of preventing the acid solution and chlorine-based solution from being brought into contact with each other without being diluted fully. The construction, arrangement, material, and forming method of separation wall are arbitrary, but the separation wall is arranged in such a manner that the liquids flowing in the first and second flow paths are not mixed. As the separation wall, for example, a plate member can be used. In this case, since the separation wall can be placed after the drum portion of the mixer has been machined into a shape symmetrical about its axis so that machining accuracy can be ensured easily, a mixer which is highly accurate even if it is small in size can be manufactured, and thus an apparatus for manufacturing sterilizing water capable of obtaining sterilizing water having a stable concentration is provided.

In the apparatus for manufacturing sterilizing water of another aspect of the present invention as well, similarly, three liquids of water, acid solution, and chlorine-based solution are fed and mixed in the feeder. Herein, the chlorine-based solution can be fed to the acid solution having been diluted with water. At this time, the acid solution and chlorine-based solution are mixed after at least the acid solution has been diluted.

Thus, the present invention provides an apparatus for manufacturing sterilizing water, in which sterilizing water is manufactured by mixing an acid solution consisting of hydrochloric acid or acetic acid or a mixture thereof and a chlorine-based solution consisting of sodium hypochlorite or chlorine dioxide or a mixture thereof with water, including a feeder, which is provided with a flow path for feeding the acid solution to a water flow to produce a dilute acid solution, for feeding the chlorine-based solution to the dilute acid solution; and a mixer which is arranged on the downstream side of the feeder to mix the water flow.

By this configuration, the dilute acid solution is prepared and then the chlorine-based solution is fed by a single feeder. In this configuration, even if one feeder is used, sterilizing water having sufficient sterilization power, for example, sterilizing water exhibiting a liquid property from weakly acid to neutral and having a hypochlorous acid concentration of about 200 ppm can be obtained. Moreover, chlorine gas is scarcely generated.

In the configuration, further, the feeder is a feeder for feeding the acid solution and the chlorine-based solution by suction utilizing a negative pressure produced in the water flow, so that the configuration can be made such that feeding using a pump is not performed.

Since a pump need not be provided in the feeding line to perform feeding, an apparatus for manufacturing sterilizing water having a simple construction can be manufactured.

In all aspects of the present invention mentioned above, the configuration can be made such that the feeder is provided with a movable portion that performs opening/closing operation of flow path for the water flow by the water supply pressure of water flow, and by the opening/closing operation, a check valve for feeding at least either of the acid solution and the chlorine-based solution is opened or closed.

If the configuration is made as described above, when the supplied water flow has a pressure not higher than a predetermined pressure, the flow shuts off, so that the acid solution and chlorine-based solution can be prevented from flowing out to the flow path. Thereby, when water scarcely flows, the acid solution and chlorine-based solution can be prevented from flowing out. Therefore, the mixing of the acid solution and the chlorine-based solution at an unintendedly high concentration can be prevented.

If this movable portion performs opening/closing operation with a fixed pressure being a threshold value by using a spring, in the apparatus for manufacturing sterilizing water in accordance with the present invention, the mixing of the acid solution and chlorine-based solution can be controlled by water supply pressure.

Also, in the above-described aspect of the present invention, the configuration may be such that the check valve provided in the path for the chlorine-based solution has this movable portion. Thereby, an apparatus for manufacturing sterilizing water, which operates well even if the number of parts is small, is provided.

In any aspect of the above-described invention, the mixer can be made a static mixer in which the water flow is mixed so that the water flow is made a substantially turbulent flow.

The expression, "the water flow is made a substantially turbulent flow" means that the water flow does not consist of a substantially laminar flow or steady vortexes only, but the water flow can be regarded as a turbulent flow by producing vortexes (Karman vortex street) changing with time. The water flow includes the flow of not only water but also liquids obtained by diluting the acid solution and chlorine-based solution.

In the above-described aspect of the present invention, the configuration can be made such that the mixer is a mixer in which mixing is performed in the water flow in a tube, and is a static mixer in which a plurality of mixing blades having different directions are arranged in the tube along the lengthwise direction of the tube, and a substantially turbulent flow is produced in the water flow in the tube by each of the mixing blades, by which the water flow is mixed.

In this case, mixing blades having different directions are manufactured so that vortexes or a turbulent flow (substantially turbulent flow) that repeatedly appears and disappears over time, such as Karman vortex street, with respect to the water flow can be generated on the downstream side of each blade. Due to the mixing blades, mixing can be performed efficiently without the production of great resistance in the flow. The mixing blade has only to generate a substantially turbulent flow. The shape of mixing blade is not subject to any special restriction if the mixing blade has a construction that generates a substantially turbulent flow. The mixing blades are arranged so as to be directed in different directions. Thereby, all parts of the water flowing in the mixer are mixed by the substantially turbulent flow, and the water flow passing through the mixing blades is fully mixed. Therefore, in the manufactured sterilizing water, variations in concentration of acid and chlorine are less liable to occur. Thus, the apparatus for manufacturing sterilizing water in accordance with the present invention can manufacture homogeneous sterilizing water capable of restraining the generation of chlorine gas.

Also, the mixing blade can have a fixed thickness. By making the thickness not smaller than a fixed value, a substantially turbulent flow such as a proper Karman vortex is induced, so that mixing can be performed satisfactorily.

In addition, the mixing blades can be manufactured by twisting a plane shaped plate member in connecting portions with narrow widths, which are provided on the plate member.

As an example of such mixing blades, a member which has narrow widths at intervals is prepared by using a plate member (for example, a plate member having the same width as the inside diameter of tube and having almost the same length as the length of tube forming the mixer), and portions having wider widths can be made mixing blades, and portions having narrower widths can be made connecting portions (refer to FIG. 5(A)). By twisting the connecting portions through a fixed angle, mixing blades in which the individual mixing blades have different directions in the tube can be manufactured easily (refer to FIG. 5(B)). Since the mixing blades have outside diameters approximately equal to the inside diameter of tube, mixing blades having high mixing ability can be manufactured easily merely by inserting the mixing blades into the tube and by fixing the end portions thereof without the use of a special support member.

The mixing blades are not necessarily limited to those shown in FIG. 5(B). The twisting angle need not necessarily be regular. Also, it is a matter of course that the apparatus for manufacturing sterilizing water in accordance with the present invention operates properly even if the mixing blades of the present invention are manufactured by other methods, for example, resin molding or three-dimensional machining.

In the present invention, means for producing the water flow is not regarded as important. An arbitrary conveying pump or suction pump can be used. Also, a water source for supplying pre-pressurized water, such as city water, may be used.

However, in all aspects of the above-described inventions, the water flow can preferably be produced by a pump located on the upstream side of the feeder. This configuration has an advantage that since the water flow can be controlled by the discharge pressure of pump, the water flow is easily stabilized. Also, since the chemical, such as acid solution and chlorine-based solution, does not come into contact with the pump, the pump need not be subjected to corrosion prevention. In the present invention, the type of pump is arbitrary, and, for example, a regenerative pump or the like can be used.

In all aspects of the above-described inventions, the chlorine-based solution can be made sodium hypochlorite, and the pH of the sterilizing water can be made in the range of 4.8 to 7.5.

If the acidity (pH) is set in the above-described range in the case of hypochlorous acid, proper sterilizing water can be realized. Also, in all apparatuses for manufacturing sterilizing water in accordance with the present invention, the above-described sterilizing water can be manufactured stably.

Also, in a method for manufacturing sterilizing water by mixing an acid solution consisting of hydrochloric acid or acetic acid or a mixture thereof and a chlorine-based solution consisting of sodium hypochlorite or chlorine dioxide or a mixture thereof with water, a method for manufacturing sterilizing water is also effective which includes a flow dividing step of separating a water flow into a first flow path and a second flow path; an acid diluting step of preparing a dilute acid solution by feeding the acid solution to the first flow path, which step follows the flow dividing step; a chlorine-base solution diluting step of preparing a dilute chlorine-based solution by feeding the chlorine-based solution to the second flow path; and a step of mixing the dilute acid solution with the dilute chlorine-based solution, which step follows the acid diluting step and the chlorine-base solution diluting step.

Also, in a method for manufacturing sterilizing water by mixing an acid solution consisting of hydrochloric acid or acetic acid or a mixture thereof and a chlorine-based solution consisting of sodium hypochlorite or chlorine dioxide or a mixture thereof with water, a method for manufacturing sterilizing water is also effective which includes an acid diluting step of preparing a dilute acid solution by feeding the acid solution to a water flow; a chlorine-based solution feeding step of feeding the chlorine-based solution, which step follows the acid diluting step; and a step of mixing the water flow, which step follows the chlorine-based solution feeding step.

In these manufacturing methods, the concentration of chlorine-based solution can be made in the range of 10 ppm to 400 ppm, preferably in the range of 100 ppm to 300 ppm. If the sterilizing water having the concentration of this range is manufactured by the above-described method, the sterilization power is high, and the construction of apparatus is simple, so that the practicability is high.

In the apparatus for manufacturing sterilizing water of another aspect of the present invention, both acid and chlorine-based solution can be mixed after being diluted with water in the feeders. At this time, the feeder is not located at a position at which the flow rate is changed by the influence of a faucet etc., and the diluted solution is once stored in a tank. This tank has a function of releasing the pressure.

That is to say, one aspect of the present invention provides an apparatus for manufacturing sterilizing water, in which sterilizing water is manufactured by feeding an acid solution consisting of hydrochloric acid or acetic acid or a mixture thereof and a chlorine-based solution consisting of sodium hypochlorite or chlorine dioxide or a mixture thereof to water, including an acid solution feeder for feeding the acid solution to a part of a water flow to produce a dilute acid solution; a dilute acid solution tank which stores the dilute acid solution and releases the supply pressure of part of the water flow; a chlorine-based solution feeder for feeding the chlorine-based solution to a remainder of the water flow to produce a dilute chlorine-based solution; a dilute chlorine-based solution tank which stores the dilute chlorine-based solution and releases the supply pressure of the remainder of the water flow; a suction water path which has two suction ports, and also has a joining portion for joining the dilute acid solution and the dilute chlorine-based solution together by sucking the dilute acid solution in the dilute acid solution tank and the dilute chlorine-based solution in the dilute chlorine-based solution tank from the two suction ports; a pump which is connected to the suction water path to suck and discharge the dilute acid solution and the dilute chlorine-based solution, which have been joined together, via the suction water path; an acid solution mixer which is provided at any position between the acid solution feeder and the pump to mix the dilute acid solution; and a chlorine-based solution mixer which is provided at any position between the chlorine-based solution feeder and the pump to mix the dilute chlorine-based solution.

By this configuration, at a position on the upstream side of the tank in which the pressure is released, a flow rate suitable for the feeding of acid solution and chlorine-based solution can be secured without depending on the quantity of sterilizing water consumed. For example, for city water, the water pressure fluctuates, and hence a change can occur in the water flow. However, the opening/closing operation of faucet for taking out sterilizing water to be used changes the water flow in a far greater range. Therefore, it is effective to inhibit the feeding of acid solution and chlorine-based solution at a position where the water flow can change depending on the usage of sterilizing water and to eliminate an influence of the change in water flow due to the usage of sterilizing water by using a tank at an intermediate position. The tank not only prevents the supply pressure from the upstream side from being transmitted to the downstream side but also prevents the usage of sterilizing water on the downstream side from affecting the water flow on the upstream side.

In this aspect, an apparatus for manufacturing sterilizing water, in which the apparatus further includes a raw water tank and at least one raw water pump for sucking raw water from the raw water tank to produce the water flow, wherein a part of the water flow and the remainder of the water flow are formed by the raw water pump, is also suitable. The raw water tank is a tank for storing city water or water from other water sources. The raw water pump may be of any type that makes the water in the raw water tank a water flow. Although the term "raw water pump" is used for convenience, in addition to a pump that sucks raw water, a pump which sucks raw water before the feeding of acidic water by sucking, for example, a dilute acidic water to which acidic water has been fed, also functions as a raw water pump. By the use of the raw water tank, even if the pressure fluctuates, for example, as in the case where the raw water is city water, fluctuations in pressure can be prevented from affecting the water flow pressure and flow velocity at the time when the acid solution and chlorine-based solution are fed.

Also, in this aspect, the raw water pump preferably includes a first raw water pump for forming the part of the water flow to which the acid solution is fed and a second raw water pump for forming the remainder of the water flow to which the chlorine-based solution is fed. If the first raw water pump and the second raw water pump are used, the part of the water flow to which the acid solution is fed and the remainder of the water flow to which the chlorine-based solution is fed can be controlled independently. Therefore, the dilution is accomplished stably, and hence the sterilizing water can be manufactured stably.

Further, in this aspect, the apparatus for manufacturing sterilizing water can be configured so that the suction water path has water paths leading from each of the two suction ports to the joining portion; the acid solution mixer is provided in the water path between the suction port, through which the dilute acid solution is sucked from the dilute acid solution tank, and the joining portion; the chlorine-based solution mixer is provided in the water path between the suction port, through which the dilute chlorine-based solution is sucked from the dilute chlorine-based solution tank, and the joining portion; and a joining mixer is further provided between the joining portion and the pump. If the mixers are arranged in this manner, sterilizing water in which mixing is performed sufficiently and homogeneous mixing is realized can be produced.

Further, the apparatus for manufacturing sterilizing water can be configured so that the acid solution mixer is provided between the acid solution feeder and the dilute acid solution tank, and the chlorine-based solution mixer is provided between the chlorine-based solution feeder and the dilute chlorine-based solution tank. Even in the case where the mixers are arranged in this manner, sterilizing water in which mixing is performed sufficiently and homogeneous mixing is realized can be produced.

In another aspect of the present invention, there is provided an apparatus for manufacturing sterilizing water, in which sterilizing water is manufactured by feeding an acid solution consisting of hydrochloric acid or acetic acid or a mixture thereof and a chlorine-based solution consisting of sodium hypochlorite or chlorine dioxide or a mixture thereof to water, including an acid solution feeder for feeding the acid solution to a water flow to produce a dilute acid solution; a dilute acid solution tank which stores the dilute acid solution and releases the supply pressure of a part of the water flow; a pump for sucking the dilute acid solution from the dilute acid solution tank; a chlorine-based solution feeder for feeding the chlorine-based solution to the water flow from the dilute acid solution tank, which is produced by the pump; an acid solution mixer which is provided at any position in a water path leading from the acid solution feeder to the chlorine-based solution feeder to mix the dilute acid solution; and a chlorine-based solution mixer which is provided at any position in a water path leading from the chlorine-based solution feeder to the pump to mix the chlorine-based solution. By storing the dilute acid solution once by using the tank in this manner, the feeding rate of acid solution that influences the pH is determined without being affected by the usage of sterilizing water.

In this aspect, it is also suitable that the apparatus for manufacturing sterilizing water further includes a raw water tank; a raw water pump for sucking raw water from the raw water tank to produce the water flow; and a sterilizing water tank for storing the manufactured sterilizing water, wherein a part of the water flow and the remainder of the water flow are formed by the raw water pump. By using the raw water tank and the raw water pump, even when the raw water is city water etc., sterilizing water can be manufactured stably without being affected by the fluctuations in pressure of the raw water.

In this configuration, the acid solution mixer can be provided between the dilute acid solution tank and the chlorine-based solution feeder. If the mixer is arranged in this manner, sterilizing water can be produced in which mixing is performed sufficiently and homogeneous mixing is realized.

Also, the acid solution mixer can be provided between the acid solution feeder and the dilute acid solution tank. If the mixer is arranged in this manner as well, sterilizing water can be produced in which mixing is performed sufficiently and homogeneous mixing is realized.

In another aspect of the present invention, there is provided an apparatus for manufacturing sterilizing water, in which sterilizing water is manufactured by feeding an acid solution consisting of hydrochloric acid or acetic acid or a mixture thereof and a chlorine-based solution consisting of sodium hypochlorite or chlorine dioxide or a mixture thereof to water, including an acid solution feeder for feeding the acid solution to a part of a water flow to produce a dilute acid solution; an acid solution mixer provided on the downstream side of the acid solution feeder; a chlorine-based solution feeder for feeding the chlorine-based solution to the remainder of the water flow to produce a dilute chlorine-based solution; a chlorine-based solution mixer provided on the downstream side of the chlorine-based solution feeder; a joining portion for joining the dilute acid solution sent from the acid solution mixer and the dilute chlorine-based solution sent from the chlorine-based solution mixer together; a joining mixer for mixing the dilute acid solution with the dilute chlorine-based solution at a position on the downstream side of the joining portion; a pump for sucking and discharging a solution mixed on the downstream side of the joining mixer; and a tank for storing sterilizing water discharged by the pump. When the tank for storing the sterilizing water is used, sterilizing water can be manufactured regardless of the usage of sterilizing water, so that the water flow need not be changed greatly depending on the usage of sterilizing water.

As another aspect of the present invention, there is provided an apparatus for manufacturing sterilizing water, in which sterilizing water is manufactured by feeding an acid solution consisting of hydrochloric acid or acetic acid or a mixture thereof and a chlorine-based solution consisting of sodium hypochlorite or chlorine dioxide or a mixture thereof to water, including a raw water tank; a raw water pump for sucking raw water from the raw water tank to produce a water flow; an acid solution feeder for feeding the acid solution to the water flow to produce a dilute acid solution; a chlorine-based solution feeder for further feeding the chlorine-based solution to the water flow; an acid solution mixer which is provided at any position in a water path leading from the acid solution feeder to the chlorine-based solution feeder to mix the dilute acid solution; a chlorine-based solution mixer which is provided at any position on the downstream side of the chlorine-based solution feeder to mix the chlorine-based solution; and a sterilizing water tank which is provided on the downstream side of the chlorine-based solution mixer to store the manufactured sterilizing water. By this configuration, by using the raw water tank and the raw water pump, even when the raw water is city water etc., sterilizing water can be manufactured stably without being affected by the fluctuations in pressure of the raw water.

In another aspect of the present invention, an apparatus for manufacturing sterilizing water, in which sterilizing water is manufactured by feeding an acid solution consisting of hydrochloric acid or acetic acid or a mixture thereof and a chlorine-based solution consisting of sodium hypochlorite or chlorine dioxide or a mixture thereof to water, including a pump for discharging raw water to produce a water flow; an acid solution feeder for feeding the acid solution to a part of a water flow to produce a dilute acid solution; an acid solution mixer provided on the downstream side of the acid solution feeder; a chlorine-based solution feeder for feeding the chlorine-based solution to the remainder of the water flow to produce a dilute chlorine-based solution; a chlorine-based solution mixer provided on the downstream side of the chlorine-based solution feeder; a joining portion for joining the dilute acid solution sent from the acid solution mixer and the dilute chlorine-based solution sent from the chlorine-based solution mixer together; a joining mixer for mixing the dilute acid solution with the dilute chlorine-based solution at a position on the downstream side of the joining portion; and a tank for storing sterilizing water manufactured by joining. In this case as well, when the tank for storing the sterilizing water is used, sterilizing water can be manufactured regardless of the usage of sterilizing water, so that the water flow need not be changed greatly depending on the usage of sterilizing water.

In each aspect of the above-described invention, the configuration can be made such that at least either of the acid solution feeder or the chlorine-based solution feeder is a feeder for feeding the acid solution or the chlorine-based solution by suction utilizing a negative pressure produced in the water flow, so that feeding using a pump is not performed. Since there is no relation between the usage of sterilizing water and the water flow because the tank is used, stable feeding is realized by using the feeder for suction feeding without performing mixing using a pump.

Also, in each aspect of the above-described invention, at least any one of the acid solution mixer, the chlorine-based solution mixer, and the joining mixer can be made a static mixer for the water flow so as to produce a substantially turbulent flow. The static mixer also operates stably since there is no relation between the usage of sterilizing water and the water flow because the tank is used. The substantially turbulent flow includes Karman vortex, a standing vortex that is considered to fully become a turbulent flow, and the like. It has only to sufficiently perform a function of mixing or agitation. Since such a turbulent flow relates closely to the velocity of water flow in the static mixer, the static mixer can be operated properly especially when there is no relation between the usage of sterilizing water and the water flow as in the present invention.

In the present invention, there is provided a static mixer including a tube serving as a water path; and many mixing elements provided in the tube so as to be arranged in the direction of a flow in the tube, characterized in that the mixing element has a joint for keeping an angular difference around the axis of the tube with respect to the adjacent mixing element; and the joint has a shape of polygon in cross section so as to provide a flexible construction such that many mixing elements are arranged along the bend of tube, and when the arrangement direction of mixing elements is bent, the mixing elements can follow the bent while the angular difference is kept. When the static mixer is made of a highly chemical resistant resin etc., if it is intended to accommodate the bend of tube by using the above-described joint, the mixer can be realized in a bent pipe. Also, the mixer can also be manufactured by using a flexible pipe.

This static mixer can be used for an apparatus for manufacturing sterilizing water using a static mixer in which the water flow is made a substantially turbulent flow and is mixed. Even such a static mixer can produce a substantially turbulent flow.

In the present invention, there is provided a regulator including a turret portion which has a plurality of flow rate restricting orifices having different inside diameters, and is capable of being turned to select any of the flow rate restricting orifices; and a turret receiving portion which rotatably holds the turret portion, and has a flow path aligning with any of the flow rate restricting orifices. The flow rate restricting orifice can be made a circular opening. The orifice is less liable to be clogged as compared with a slit achieving the same flow rate restricting effect, and less liable to exert an adverse influence such that strain etc. of material due to a temperature change cause a change in flow rate.

The apparatus for manufacturing sterilizing water may be configured so that this regulator is inserted in at least either of the flow paths for the acid solution and the chlorine-based solution fed by either feeder. The above-described regulator is suitable for regulating the feeding of the acid solution and chlorine-based solution of a very low flow rate as in the sterilizing water described in the aspects of the present invention.

In the present invention, there is provided a flow sensor including a cylindrical piston member which is made of a material having light transmitting properties, and moves in the axial direction; a cylinder portion which movably holds the piston member with the axial direction of the piston member being directed in the substantially vertical direction, has a cylindrical inside side surface, and is provided with a plurality of minute holes arranged in the inside side surface so that the minute holes serve as a flow path in succession according to the axial displacement of the piston member; a front chamber and a rear chamber which are separated from each other by the cylinder portion and the piston member, and are connected to each other by the minute holes; a light intercepting member which moves together with the piston member; a light emitting element which emits either light of ultraviolet rays, visible rays, and infrared rays, and is arranged so that a light path is formed in the range in which the light intercepting member moves with the light being used as detection light; and a light receiving element which is arranged to receive the light of the light emitting element so that it can be detected that the light intercepting member is located in the light path, characterized in that the flow sensor is used in an orientation such that when the piston member moves downward due to gravity, the minute holes are closed; when a differential pressure obtained by removing the pressure of working fluid in the rear chamber from the pressure of working fluid in the front chamber is not higher than a predetermined working pressure, a movable member consisting of the light intercepting member and the piston member closes at least some of the minute holes, and when the differential pressure becomes higher than the predetermined working pressure, the movable member moves upward according to the differential pressure, and operates so as to open the closed minute holes in succession to cause a large quantity of working fluid to flow from the front chamber to the rear chamber; and a change in the detected light quantity produced by the interception of the light path caused by the light intercepting portion of the movable member moved by a change in the differential pressure is detected by the light receiving element, and the flow rate of the working fluid is detected based on a change in the output signal. Such a flow sensor can be manufactured at a low cost. In particular, if a portion that is in contact with the liquid is made of a resin, the flow sensor can operate stably. Also, the flow sensor can detect the flow sensitively even if the flow rate is very low.

In the apparatus for manufacturing sterilizing water in accordance with the present invention, an electromagnetic valve capable of shutting off the outflow of sterilizing water is further provided in at least either water path; and the electromagnetic valve can be controlled according to the output signal by using this flow sensor in the flow path for the chemical fed by either feeder. By using an inexpensive and sensitive flow sensor having high chemical resistance, the apparatus for manufacturing sterilizing water in accordance with the present invention can gain high practicability at a low cost.

In all aspects of the present invention, the type of pump is arbitrary, and, for example, a regenerative pump or the like can be used.

Also, the chlorine-based solution can be made sodium hypochlorite, and the pH of the sterilizing water can be made in the range of 4.8 to 7.5. If the acidity (pH) is set in the above-described range in the case of hypochlorous acid, proper sterilizing water can be realized. Also, in all apparatuses for manufacturing sterilizing water in accordance with the present invention, the above-described sterilizing water can be manufactured stably.

Also, in a method for manufacturing sterilizing water by mixing an acid solution consisting of hydrochloric acid or acetic acid or a mixture thereof and a chlorine-based solution consisting of sodium hypochlorite or chlorine dioxide or a mixture thereof with water, a method for manufacturing sterilizing water is also effective which includes a flow dividing step of separating a water flow into a first flow path and a second flow path; an acid diluting step of preparing a dilute acid solution by feeding the acid to the first flow path, which step follows the flow dividing step; a chlorine-base solution diluting step of preparing a dilute chlorine-based solution by feeding the chlorine-based solution to the second flow path; and a step of mixing the dilute acid solution with the dilute chlorine-based solution, which step follows the acid diluting step and the chlorine-base solution diluting step.

Also, in a method for manufacturing sterilizing water by mixing an acid solution consisting of hydrochloric acid or acetic acid or a mixture thereof and a chlorine-based solution consisting of sodium hypochlorite or chlorine dioxide or a mixture thereof with water, a method for manufacturing sterilizing water is also effective which includes an acid diluting step of preparing a dilute acid solution by feeding the acid to a water flow; a chlorine-based solution feeding step of feeding the chlorine-based solution, which step follows the acid diluting step; and a step of mixing the water flow, which step follows the chlorine-based solution feeding step.

In these manufacturing methods, the concentration of chlorine-based solution can be made in the range of 10 ppm to 400 ppm, preferably in the range of 100 ppm to 300 ppm. If sterilizing water having a concentration in this range is manufactured by the above-described method, its sterilization power is high, and the construction of its apparatus is simple, so that the practicability is high.

In the present invention, there is provided an apparatus for manufacturing sterilizing water, in which sterilizing water is manufactured by feeding an acid solution consisting of hydrochloric acid or acetic acid or a mixture thereof and a chlorine-based solution consisting of sodium hypochlorite or chlorine dioxide or a mixture thereof to water, including a first water path; a first feeder, which is provided in the first water path, for feeding the acid solution; a second water path, which is divided from the first water path at a position on the upstream side of the first feeder and is returned to the first water path at a position on the downstream side of the first feeder; a second feeder, which is provided in the second water path, for feeding the chlorine-based solution; a first bypass water path which is divided from the first water path and is returned to the first water path to bypass the first feeder; a second bypass water path which is divided from the second water path and is returned to the second water path to bypass the second feeder; a first flow rate restricting valve provided in the first bypass water path; a second flow rate restricting valve provided in the second bypass water path; and a sterilizing water tank for receiving a water flow in the first water path.

Also, in the present invention, there is provided an apparatus for manufacturing sterilizing water, in which sterilizing water is manufactured by feeding an acid solution consisting of hydrochloric acid or acetic acid or a mixture thereof and a chlorine-based solution consisting of sodium hypochlorite or chlorine dioxide or a mixture thereof to water, including a main water path; a first feeder, which is provided in the main water path, for feeding the acid solution to a water flow; a second feeder, which is provided in the main water flow so as to be located on the downstream side of the first feeder, for feeding the chlorine-based solution; a first bypass water path which is divided from the main water path and is returned to the main water path to bypass the first feeder; a second bypass water path which is divided from the main water path and is returned to the main water path to bypass the second feeder; a first flow rate restricting valve provided in the first bypass water path; a second flow rate restricting valve provided in the second bypass water path; and a sterilizing water tank for receiving a water flow in the main water path.

If the bypass water path arranged in parallel with the feeder is used, and the flow rate restricting valve is further provided in the bypass water path, the flow rate in the bypass water path can be adjusted by fully opening, partially opening, or fully closing the valve. In particular, if the bypass water path is provided for each feeder, the feeding using the feeder can be controlled by adjusting the flow rate restricting valve in the bypass water path, so that satisfactory feeding is realized. In the above-described apparatus for manufacturing sterilizing water, by the above-described configuration, the feeder is operated under a condition suitable for feeding, and the concentration of acid solution and chlorine-based solution in the water flow can be decreased by using the bypass water path. Therefore, the operations of feeding and dilution can be set so as to meet the respective objectives, so that the stable operation can be performed. Also, by adjusting the flow rate in the bypass water path at the time when the apparatus for manufacturing sterilizing water is installed, the manufacturing conditions for the sterilizing water can be kept proper even if the raw water for producing the sterilizing water has various water quality, supply quantities, or pressures.

The sterilizing water tank can be configured so that a vessel having a certain overflow level is provided; at least any of the water paths leading to the sterilizing water tank has an outflow port arranged below the overflow level in the vessel; and the sterilizing water tank stores the liquid overflowing the vessel.

When the sterilizing water tank is used, it is effective to use a vessel which stores liquid therein to a certain volume and overflows if the liquid is further added (for example, a vessel whose upper side is open, a vessel provided with an outflow port in the side surface thereof). If the water path for causing the liquid to flow to the sterilizing water tank has an outflow port disposed at an inside position lower than the overflow level of the vessel, the water pressure applied to the outflow port of the water path is fixed regardless of the quantity of sterilizing water stored in the sterilizing water tank. Moreover, no air intrudes from the outflow port of water path even when the apparatus is shut down. Therefore, the pressure on the downstream side of the suction type feeder provided in the water path is stabilized, and hence the feeding operation of the suction type feeder is stabilized.

BRIEF DESCRIPTION OF THE DRAWINGS

FIG. 5 is a schematic view showing a configuration and operation of mixing blades of a mixer in accordance with an example of the present invention;

DETAILED DESCRIPTION OF EMBODIMENTS OF THE INVENTION

Embodiments of the present invention will now be described in detail.

First Embodiment

Figure 1:
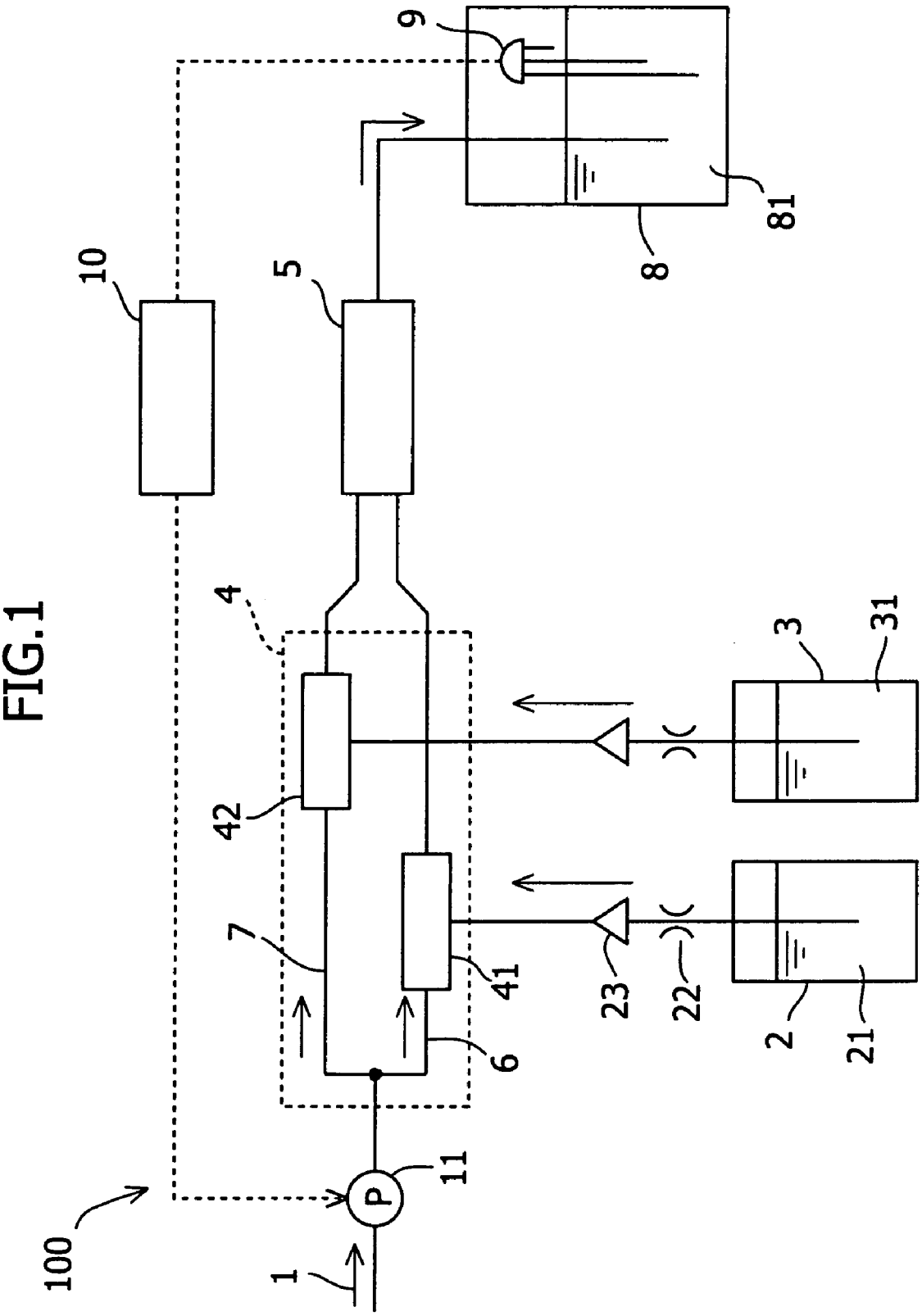
FIG. 1 is a system diagram showing a configuration of an apparatus for manufacturing sterilizing water in accordance with one embodiment of the present invention.

An embodiment of the present invention will be described. FIG. 1 is a schematic system view of an apparatus 100 for manufacturing sterilizing water in accordance with one embodiment of the present invention.

In the apparatus 100 for manufacturing sterilizing water, raw water 1 is sucked and supplied under pressure by a suitable pump 11, and to the supplied raw water 1, an acid solution 21 is fed from an acid tank 2 to form an acidic water, and further a chlorine-based solution 31 is fed from a chlorine-based solution tank 3, by which sterilizing water is manufactured. The configuration is such that the quantity of feeding of the acid solution 21 is controlled by a flow rate regulating portion 22, and when the water flow is shut off by a check valve 23, a flow path 6 is isolated from the acid tank 2.

The raw water 1 is not subject to any special restriction, and pure water, city water, river water, underground water, and the like are suitably used according to the application. As the acid solution 21, hydrochloric acid (hydrogen chloride solution) with a suitable concentration (for example, 8.5%), acetic acid, and the like are used. Also, as the chlorine-based solution 31, sodium hypochlorite solution with a suitable concentration (for example, 12%), chlorine dioxide, and the like are used.

The raw water 1 is divided by a first flow path 6 and a second flow path 7, and the acid solution 21 and the chlorine-based solution 31 are fed to each of the divided raw water 1. The acid solution 21 is fed to the raw water in a feeding portion 41 and diluted to yield a dilute acid solution. Also, the chlorine-based solution 31 is fed to the raw water in a feeding portion 42 and diluted to yield a dilute chlorine-based solution. The dilute acid solution and the dilute chlorine-based solution are mixed with each other in a mixer 5 provided on the downstream side of the feeding portions 41 and 42, by which sterilizing water 81 containing water, acid solution, and chlorine-based solution is manufactured. The sterilizing water 81 may be stored in a tank 8. Alternatively, the sterilizing water 81 may be used directly as sterilizing water. When the sterilizing water 81 is stored in the tank 8, the quantity of sterilizing water in the tank is detected by a liquid level sensor 9, and the pump 11 is controlled by control means 10 so that a fixed quantity of sterilizing water can be maintained.

In this embodiment, both of the feeding portion 41 and the feeding portion 42 are provided in a feeder 4. The feeder 4 includes both of the first flow path 7 for feeding the acid solution to the raw water 1 and the second flow path 6.

(General Explanation of Example)

Figure 2:
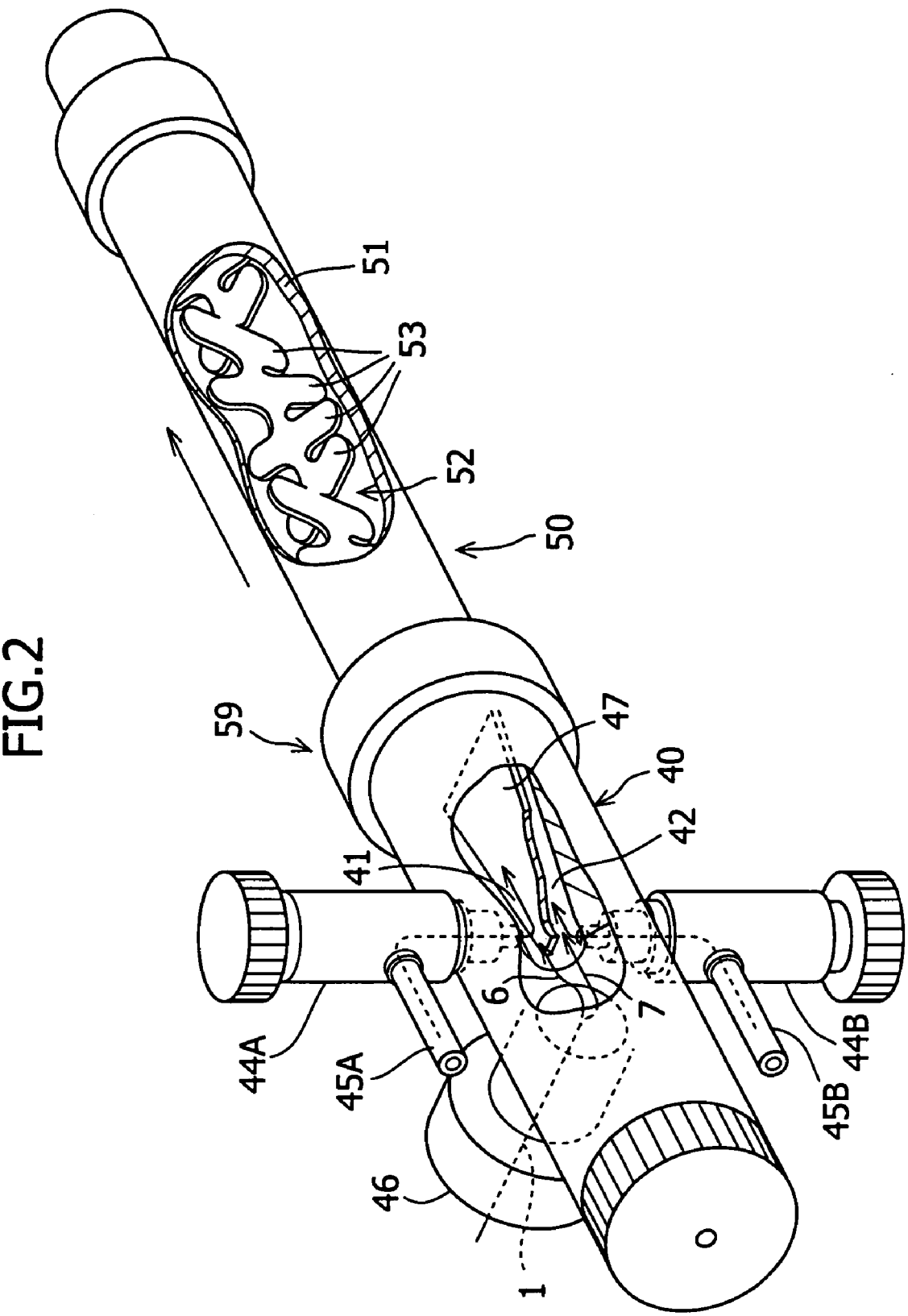
FIG. 2 is a partially cutaway perspective view showing schematic constructions of a feeder and a mixer in accordance with an example of the present invention.

Next, examples of the feeder 4 and the mixer 5 that realize the embodiment used for the apparatus for manufacturing sterilizing water shown in the system diagram as shown in FIG. 1 will be explained with reference to FIGS. 2 and 3. FIG. 2 is a partially cutaway perspective view showing schematic constructions of the feeder 40 and the mixer 50 of this example. In this example, the feeder 40 and the mixer 50 both have a cylindrical appearance, and are connected to each other by a connecting portion 59. Also, FIG. 3 is a sectional view showing constructions of the feeder 40 and the mixer 50.

(Explanation of Feeder)

The feeder 40 of this example is provided with a raw water flange portion 46 serving as an introduction port of water and chemical introduction assemblies 44A and 44B. The chemical introduction assemblies 44A and 44B are provided with chemical introduction ports 45A and 45B for receiving the acid solution and chlorine-based solution, respectively. In a drum portion 43 of the feeder 40, a movable valve (movable part) 48 is provided. The movable valve (movable part) 48 is urged toward a tip end portion 483 of the movable valve 48 by a coil spring 482.

Figure 3:
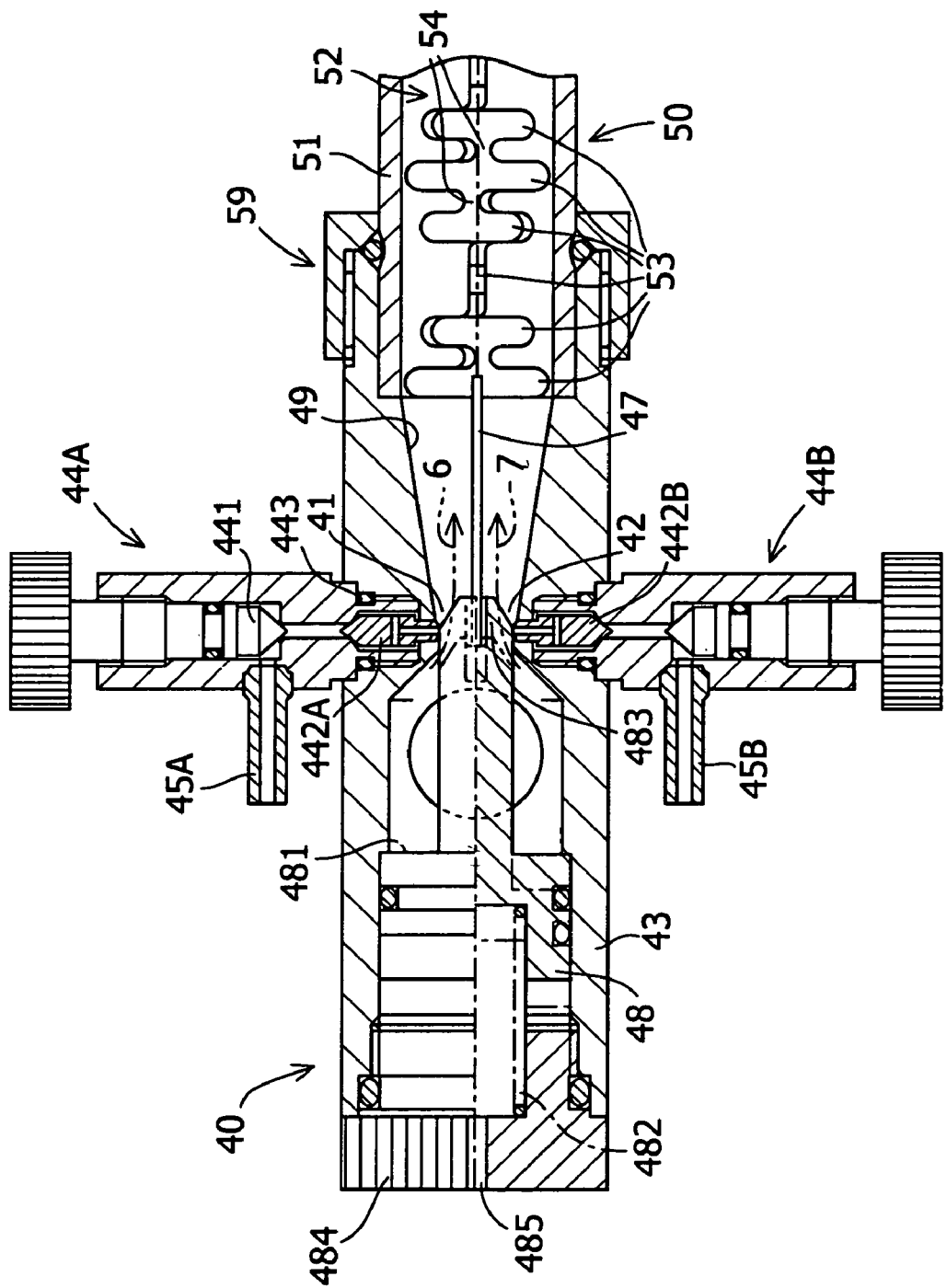
FIG. 3 is a sectional view showing constructions of a feeder and a mixer in accordance with an example of the present invention.

When the raw water 1 is supplied under pressure, the movable valve (movable part) 48 moves so that the raw water 1 is allowed to flow in the first flow path 6 and the second flow path 7 by the compression of the coil spring 48 under the pressure of raw water received by a surface 481 (imaginary line in FIG. 3, open position). The coil spring 482 is fixed to the drum portion 43 by an end cap 484. This end cap 484 is formed with a leak hole 485 to let the back pressure of the movable valve 48 escape into the atmosphere.

In the vicinity of the first and second flow paths 6 and 7 thus secured, the water flow is throttled, so that the flow velocity of water flow increases, and hence the acid solution and chlorine-based solution are introduced through check valves 442A and 442B of the chemical introduction assembly 44A in accordance with Bernoulli theorem. When the movable valve 48 is at an open position, both of the check valves 442A and 442B are in an open state. Since the feed positions correspond to the feeding portions 41 and 42 in FIG. 1, in FIG. 2 as well, the same reference numerals are used and the feed positions are indicated as the feeding portions 41 and 42.

At this time, the raw water 1 supplied from the raw water flange portion 46 flows, in the mixer 40, dividedly in the first flow path 6 defined as one side of a separation wall 47 and the second flow path 7 defined as the other side of the separation wall 47. In FIGS. 2 and 3, the first flow path 6 and the second flow path 7 are indicated as the upper side and the lower side of the separation wall 47, respectively. To the water flows in these flow paths, the acid solution and chlorine-based solution are fed from the two chemical introduction assemblies 44A and 44B, respectively. The acid solution and chlorine-based solution flowing through the first flow path and the second flow path, respectively, do not mix with each other in the feeder. Thus, in the feeder 40 of this example, the first flow path and the second flow path are provided, and the acid solution and chlorine-based solution are fed to the water flows in these flow paths and are diluted within separated streams. Feeding is accomplished by a negative pressure occurring according to the flow velocity of water flow, so that a pump dedicated to feeding the acid solution and chlorine-based solution is not needed.

Also, in this example, the movable valve 48 is arranged so that when the supply pressure of the raw water 1 is lower than a predetermined value, the tip end portion 483 thereof shuts off the first flow path 6 and the second flow path 7 (solid-line position in FIG. 3, closed position). At this time, the check valves 442A and 442B of the chemical introduction assemblies 44A and 44B are further pushed in by the tip end portion 483 of the movable valve 48, so that the acid solution and chlorine-based solution are shut off from the first flow path 6 and the second flow path 7, respectively. Thereby, when the supply pressure of the raw water 1 is lower than a constant pressure, not only the raw water is shut off but also the feeding of acid solution and chlorine-based solution is shut off. The dilute acid solution and dilute chlorine-based solution, which have been diluted in the feeding portion 41 and the feeding portion 42 in the first flow path 6 and the second flow path 7, respectively, pass through a skirt portion 49 with an opening taper angle of 8 degrees to decrease the flow velocity, and then flow out to the mixer 50 connected to the downstream side of the feeder 40.

(Explanation of Chemical Introduction Assembly)

Figure 4:
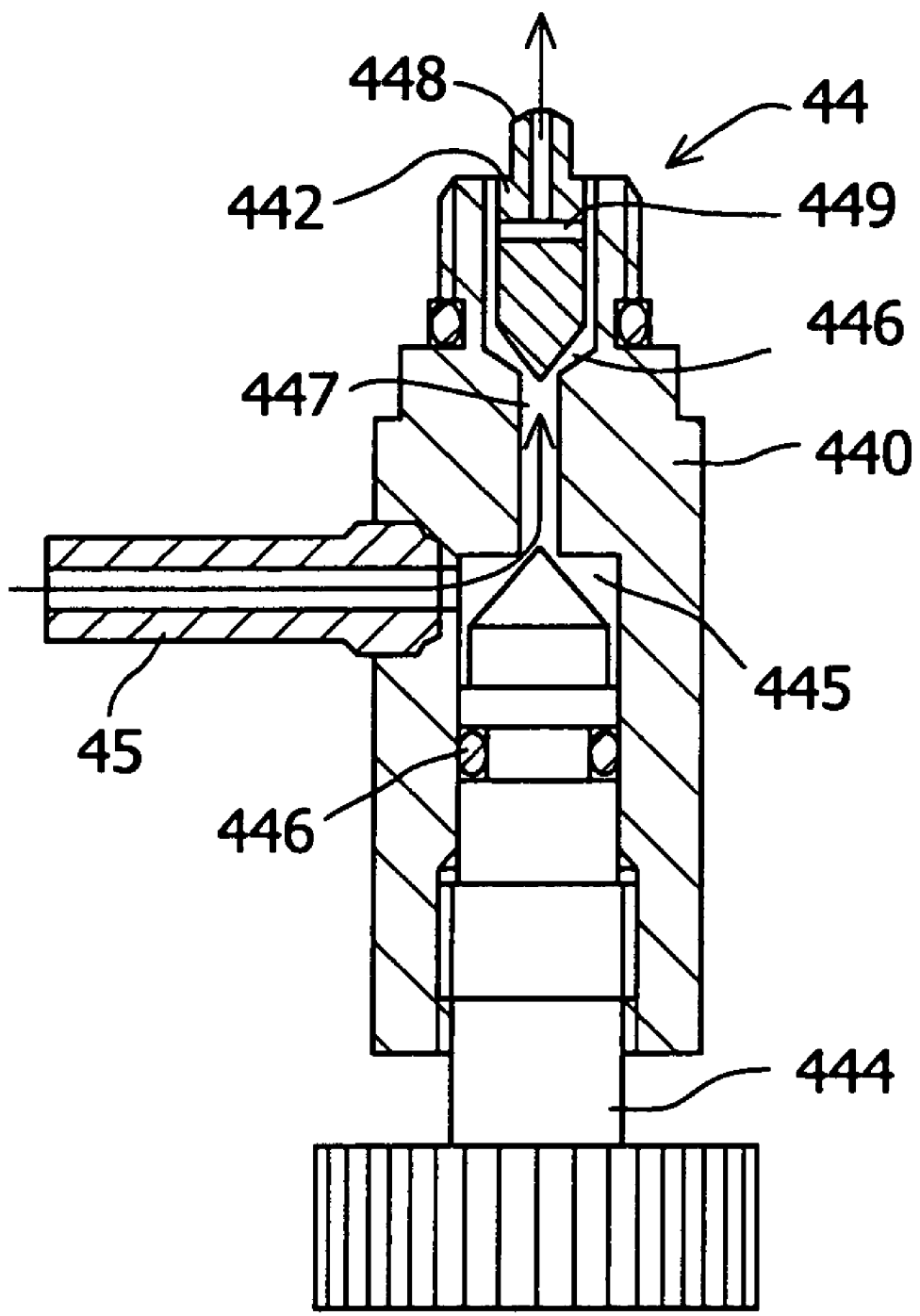
FIG. 4 is a sectional view showing a construction of a chemical introduction assembly in accordance with an example of the present invention.

The chemical introduction assembly 44A, 44B (hereinafter, collectively indicated as 44) combined with the feeder 40 includes a cylindrical drum portion 440, the chemical introduction port 45, the check valve 442, the flow rate regulating screw 444, and the 0-ring 446 for the flow rate regulating screw 444 (FIG. 4). The cylindrical drum portion 440 is fitted threadedly with the chemical introduction port 45. The chemical introduction port 45 contains a flow path therein. The chemical sent through this flow path is introduced into a flow rate regulating screw containing portion provided in the drum portion 440, and flows in a chemical flow path 447 extending along the axis of the drum portion 440. The flow rate regulating screw 444 is screwed in the drum portion 440 so as to be capable of regulating the flow rate of chemical in the chemical flow path 447 by a tip end portion 445 of the flow rate regulating screw 444 by turning the screw, and is sealed by the suitable O-ring 446. The chemical, such as acid solution and chlorine-based solution, flowing in the chemical flow path 447 flows into the check valve 442, and flows out of a chemical flow path 449 in the check valve 442. The check valve 442 is configured so that when the tip end portion 483 (FIG. 3) of the movable part 48 pushes in a tip end portion 448 of the check valve 442, an opening/closing portion 446 formed between the check valve 442 and the drum portion 440 is shut off, by which the flow path for the chemical is shut off.

(Explanation of Mixer)

Also, the mixer 50 in this example receives solutions diluted as described above of acid solution and chlorine-based solution (FIGS. 2 and 3). For the mixer 50, a pipe portion 51 is connected to an outflow port of the feeder 40 by the connecting portion 59 in such a manner that the liquid does not leak. In the pipe portion 51, a mixing blade body 52 having many mixing blades 53 is provided. The mixing blade body 52 is arranged so that the position thereof is fixed with respect to the pipe portion 51. By a structural feature, described later, the individual mixing blades 53 cause turbulence in the water flow, by which the solutions are strongly mixed so that the concentration of solute etc. is uniform.

As seen in FIG. 3, a downstream end of the separation wall 47 is connected to the mixing blades 53.

(Construction of Blade of Mixer)

For the mixer 50, which is an example of the mixer, the mixing blade body 52 is made of a plate member. This plate member extends in the lengthwise direction of the pipe portion 51, and has a width that is accommodated in the inside diameter of the pipe portion 51. The plate member is first fabricated into a shape having constricted parts at a fixed lengthwise intervals (refer to FIG. 5(A)). This fabrication can be accomplished by using an arbitrary fabricating means (for example, punching). In this example, as the plate member, one stainless steel sheet with a thickness of 2 mm is used. Next, the plate member of this shape is twisted at the constricted parts with the lengthwise direction being the axis of twisting (refer to FIG. 5(B)). Thereby, the mixing blade body 52 having a plurality of mixing blades 53 connected to each other by connecting parts 54 as shown in FIG. 3 is manufactured.

The mixing blades 53 of the mixing blade body 52 are arranged so that a main surface 531 of the mixing blade 53 extends along the water flow in the mixer, and the mixing blade 53 itself is not directed slantwise with respect to the flow. However, when the mixing blades 53 are arranged in the water flow, a Karman vortex street is formed on the downstream side of water flow (FIG. 5(C)). This Karman vortex street is produced in succession with time and flows to the downstream side together with the water flow, and the individual vortex itself is not fixed at a given position. The vortex street continues to be formed in succession on the downstream side of the mixing blade 52. This Karman vortex street has a property that the time period of formation becomes short as the flow velocity of water flowing there increases. Further, when the flow velocity of water flow increases, the Karman vortex street changes to an almost complete turbulent flow. In this example, the operation pressure of the movable valve 48 is set so that at least the Karman vortex street is formed in the case where the water supply pressure is such that the movable valve 48 is at an open position.

The directions of the individual mixing blades 53 forming the Karman vortex street are different (FIG. 5(B)). Therefore, the water flow in the pipe 51 of the mixer 50 is fully mixed at any given cross-sectional position in the pipe 51 of the water flow. The same is true for the case where the flow velocity is higher and a turbulent flow is formed.

Although this example discloses a particular material, manufacturing method, and shape of the mixer, the material, manufacturing method, and shape thereof can be changed. For example, the mixing blade body of the same shape can be made of a plastic. Also, regarding the change of manufacturing method, for example, the mixing blade body of the same shape can be made by machining. Also, regarding the change of shape, in place of the mixing blades twisted so as to have a fixed angular difference as shown in this example, the mixing blades can take a shape such as to have a random angular difference. Also, the shape of individual blade may be, for example, circular or triangular in cross section, not being the plate shape as in the above-described example. Anyway, any mixing blade body in which the directions of the mixing blades are different so that each mixing blade produces a substantially turbulent flow in the water flow can be used as the means of the present invention.

By the feeder and mixer of the above-described examples, an apparatus for manufacturing sterilizing water, which can manufacture sterilizing water stably using the feeder capable of feeding three liquids and has a simple construction, could be manufactured.

Second Embodiment

Figure 6:
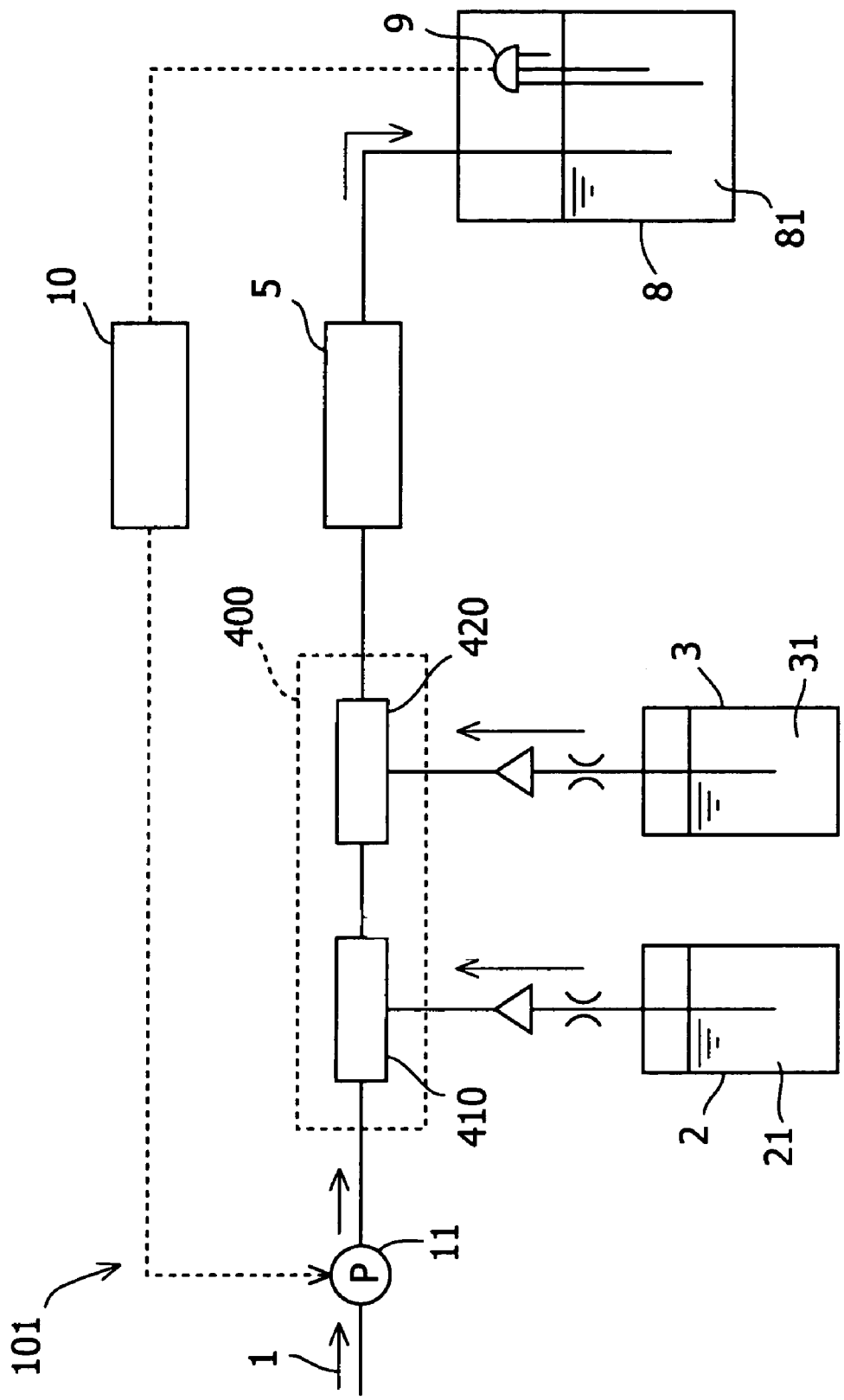
FIG. 6 is a system diagram showing a configuration of an apparatus for manufacturing sterilizing water in accordance with another embodiment of the present invention.

Another embodiment of the present invention will be described. FIG. 6 is a schematic system view of an apparatus 101 for manufacturing sterilizing water in accordance with another embodiment of the present invention.

In the apparatus 101 for manufacturing sterilizing water, as in the apparatus 100 for manufacturing sterilizing water, the raw water 1 is sucked and supplied under pressure by the suitable pump 11, and to the supplied raw water 1, the acid solution 21 is fed from the acid tank 2 to form the dilute acid solution, and further the chlorine-based solution 31 is fed from the chlorine-based solution tank 3, by which sterilizing water is manufactured.

In this embodiment, unlike the above-described first embodiment, the raw water 1 flows in a series of flow path, not in plural flow paths. The acid solution 21 and the chlorine-based solution 31 are fed in this order to the raw water 1 flowing in the flow path. The acid solution 21 is fed to the raw water in a feeding portion 410 and diluted, by which the dilute acid solution is yielded, and then the chlorine-based solution 31 is fed in a feeding portion 420. The sterilizing water is mixed in the mixer 5 provided on the downstream side of the feeding portions 410 and 420, by which the sterilizing water 81 containing water, acid solution, and chlorine-based solution is manufactured. As in the above-described first embodiment, the tank 8, the liquid level sensor 9, and the control means 10 are used, and the pump 11 is controlled by the control means 10. In the second embodiment, both of the aforementioned feeding portions 410 and 420 are provided in a feeder 400.

(General Explanation of Example)

Figure 7:
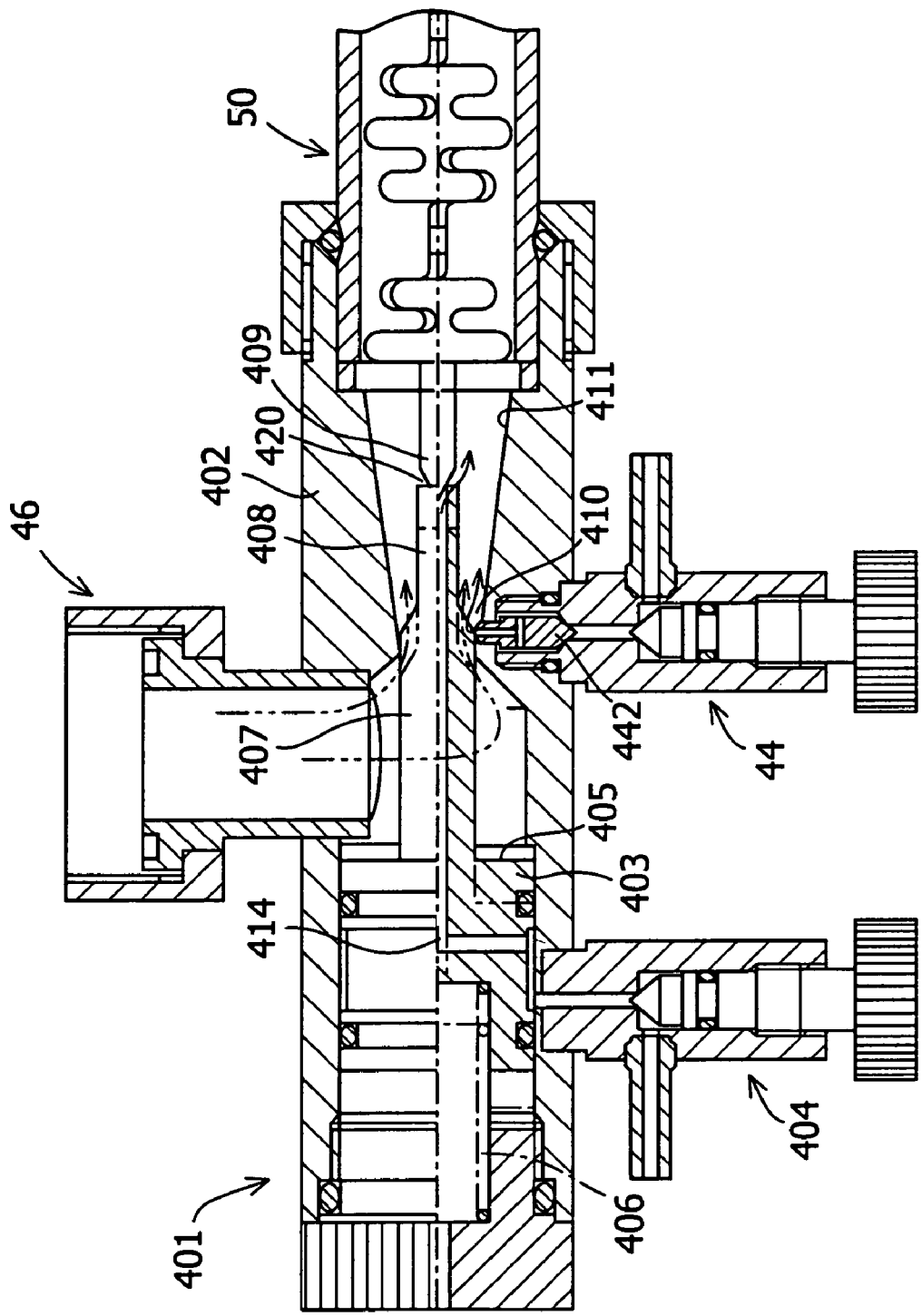
FIG. 7 is a sectional view showing constructions of a feeder and a mixer in accordance with an example of the present invention.

Next, an example of the feeder 401 that realizes this embodiment will be explained with reference to FIG. 7. FIG. 7 is a sectional view showing constructions of the feeder 401 of this example and the mixer 50. The feeding portion 410 in which the acid solution is fed corresponds to the outlet of the chemical introduction assembly 44, and the feeding portion 420 in which the chlorine-based solution is fed corresponds to the outlet of a tip end portion 408 of a movable valve 403.

(Explanation of Feeder)

The feeder 401 is provided with the raw water flange portion 46 serving as an introduction port of water and chemical introduction assemblies 44 and 404. The chemical introduction assembly 44 is constructed in the same way as the chemical introduction assembly 44A explained in the above-described example. The chemical introduction assembly 404 has no check valve, and is attached to a drum portion 402 of the feeder 401 to introduce the chemical into the movable valve (movable part) 403 provided in the drum portion 402.

When the raw water 1 is supplied, as in the above-described example, the movable valve (movable part) 403 compresses a coil spring 406 under the pressure of raw water received by a surface 405. At this time, a shoulder portion 407 of the movable valve 403 is arranged at a position such as not to shut off the flow path, so that the acid solution is fed from the tip end portion of the check valve 442 of the chemical introduction assembly 44. Also, the tip end portion 408 of the movable valve 403 is arranged at a position separated from a movable valve stopper 409, so that the chlorine-based solution is fed from a chemical flow path 414 formed in the movable valve 403 (imaginary line in FIG. 7, open position).

The movable valve 403 is provided with the chemical flow path 414 in the central portion thereof. The chemical introduced from the chemical introduction assembly 404 flows in the chemical flow path 414, and flows out of the tip end of the movable valve 403. In the vicinity of the tip end portion of the check valve 442 of the chemical introduction assembly 44 and in the vicinity of the outlet of the chemical flow path 414, the acid solution and the chlorine-based solution are sucked by the water flow and fed to the water flow. The positions at which the chemicals are fed correspond to the feeding portions 410 and 420 in FIG. 1, so that in FIG. 7 as well, the feeding portions are indicated by the same reference numbers 410 and 420.

Inside the feeder 401 of this example, a series of flow paths for water flow are provided. In the feeder 401, the acid solution is first fed to the water and diluted, and on the downstream side, the chlorine-based solution is fed. These chemicals are fed by suction utilizing a negative pressure produced by the water flow and diluted. As in the above-described first embodiment, since the acid solution and chlorine-based solution can be fed to the water flow by the negative pressure, a pump dedicated to feeding the acid solution and chlorine-based solution is not needed.

Also, in this example as well, when the supply pressure of the raw water 1 is lower than a predetermined value, the movable valve (movable part) 403 is urged by the coil spring 406, so that the tip end portion 408 of the movable valve 403 shuts off the flow path for the chlorine-based solution, and the shoulder portion 407 of the movable valve 403 shuts off the flow path for acid solution in cooperation with the check valve 442 (solid-line position in FIG. 7, closed position). The operations of the chemical introduction assembly 44 and the check valve 442 provided therein are the same as those in the above-described example. The tip end of the movable valve stopper 409 fits in the outlet of the chemical flow path 414 in the tip end portion 408 of the movable valve 403, so that the chlorine-based solution does not flow out of the chemical flow path 414. Thus, when the supply pressure of the raw water 1 is lower than a constant value, not only the supply of raw water is shut off, but also the supply of acid solution and chlorine-based solution is also shut off.

The objects, constructions, and operations of the chemical introduction assembly 44 and the mixer 50, which are used in this example, are the same as those in the above-described example.

By using the feeder and mixer of these examples, an apparatus for manufacturing sterilizing water having a series of flow path shown in FIG. 6, which uses the feeder capable of feeding three liquids and has a simple construction, could be manufactured. Thereby, sterilizing water could be manufactured stably and easily.

Third Embodiment

Next, the case where the concentration of chlorine-based solution is changed in the apparatus for manufacturing sterilizing water in accordance with the present invention will be explained.

In this embodiment, the properties of sterilizing water were studied by changing the concentration of chlorine-based solution by changing the dilution ratio thereof. In the present invention, as the chlorine-based solution before dilution, a sodium hypochlorite solution with a concentration of 12% was used, and as the apparatus for manufacturing sterilizing water, an apparatus having a system shown in FIG. 1 and being provided with the feeder and mixer of the examples shown in FIGS. 2 and 3 was used.

The final concentration of chlorine-based solution and the sterilization power at each concentration were evaluated for each dilution ratio as given in Table 1.

TABLE 1

| Dilution ratio (times) | 12000 | 1200 | 400 | 300 | 100 |
| Concentration (ppm) | 10 | 100 | 300 | 400 | 1200 |
| Sterilization power | Normal | Enough | Enough | Strong | Strong |

As the sterilization power, an indicator of sterilization power used in the field of foods is shown. The indicator of "normal" indicates sterilization power corresponding to a chlorine concentration of 1000 ppm in the case where the liquid properties are not adjusted by an acid solution. "Enough" indicates sterilization power higher than the normal power, which was high enough for the sterilizing water to be applied to the field of foods. Also, "strong" indicates sterilization power having a strength that would not be usually needed in the field of foods.

The sterilizing water thus manufactured, in which the concentration of sodium hypochlorite was 1200 ppm, emitted a strong chlorine odor at the time of actual use, so that it was unsuitable for applications in which it was used for long-term work. The reason for this was that in the apparatus for manufacturing sterilizing water in accordance with the present invention, a water flow including some heterogeneity was mixed with acid solution and chlorine-based solution by the mixer. Thereby, the manufacturing conditions of sterilizing water were somewhat varied, and a chlorine odor was noticed, for example, especially at the time of opening/closing of the movable valve 48.

Contrarily, the sterilizing water with sodium hypochlorite concentrations of 100, 300 and 400 ppm had no chlorine odor and could be used in applications in which it was used for long-term work. Also, the sterilizing water with a sodium hypochlorite concentration of 10 ppm exhibited sterilization power of almost the same degree as the conventional case of 1000 ppm concentration in which the liquid properties were not regulated by acid solution, but it had a weak chlorine odor and was useful, for example, in an application in which sterilization was accomplished by long-term immersion.

Fourth Embodiment

Figure 8:
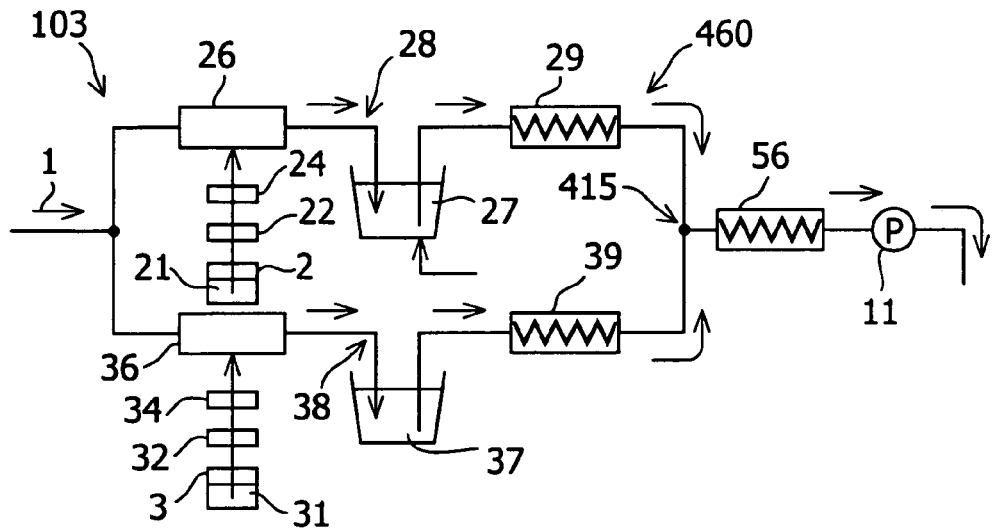
FIG. 8 is a system diagram showing a configuration of an apparatus for manufacturing sterilizing water in accordance with still another embodiment of the present invention.

Still another embodiment of the present invention will be explained. FIG. 8 is a system diagram showing a configuration of an apparatus 103 for manufacturing sterilizing water in accordance with one embodiment of the present invention. In this embodiment, separate feeders are used for feeding the acid solution and chlorine-based solution.

In the apparatus 103 for manufacturing sterilizing water, the raw water 1 is supplied under pressure by suitable means. The water flow of the raw water 1 is divided into two water flows. For one water flow, the acid solution 21 is fed to the water flow from the acid solution tank 2 by an acid solution feeder 26, and the dilute acid solution (acidic water) is stored in a dilute acid solution tank 27. For the other water flow, the chlorine-based solution 31 is fed to the water flow from the chlorine-based solution tank 3 by a chlorine-based solution feeder 36, and the dilute chlorine-based solution is stored in a dilute chlorine-based solution tank 37. On the suction side of the pump 11, a suction water path 460 is installed. This suction water path 460 has two suction ports, and the suction ports each are arranged in the dilute acid solution tank 27 and the dilute chlorine-based solution tank 37. The dilute acid solution and the dilute chlorine-based solution are sucked through the suction ports, and are joined together in a joining portion 415. An acid solution mixer 29 and a chlorine-based solution mixer 39 are provided between the pump and the acid solution feeder 26 and between the pump and the chlorine-based solution feeder 36, respectively.

FIG. 8 shows one example of such an arrangement. In the suction water path 460 shown in FIG. 8, the acid solution mixer 29 and the chlorine-based solution mixer 39 are arranged in the water paths between the suction port and the joining portion 415, and a joining mixer 56 is provided between the joining portion 415 and the pump 11. The sterilizing water manufactured by joining is taken out through a faucet (not shown) etc. provided in the water path on the downstream side of the pump.

Figure 16:
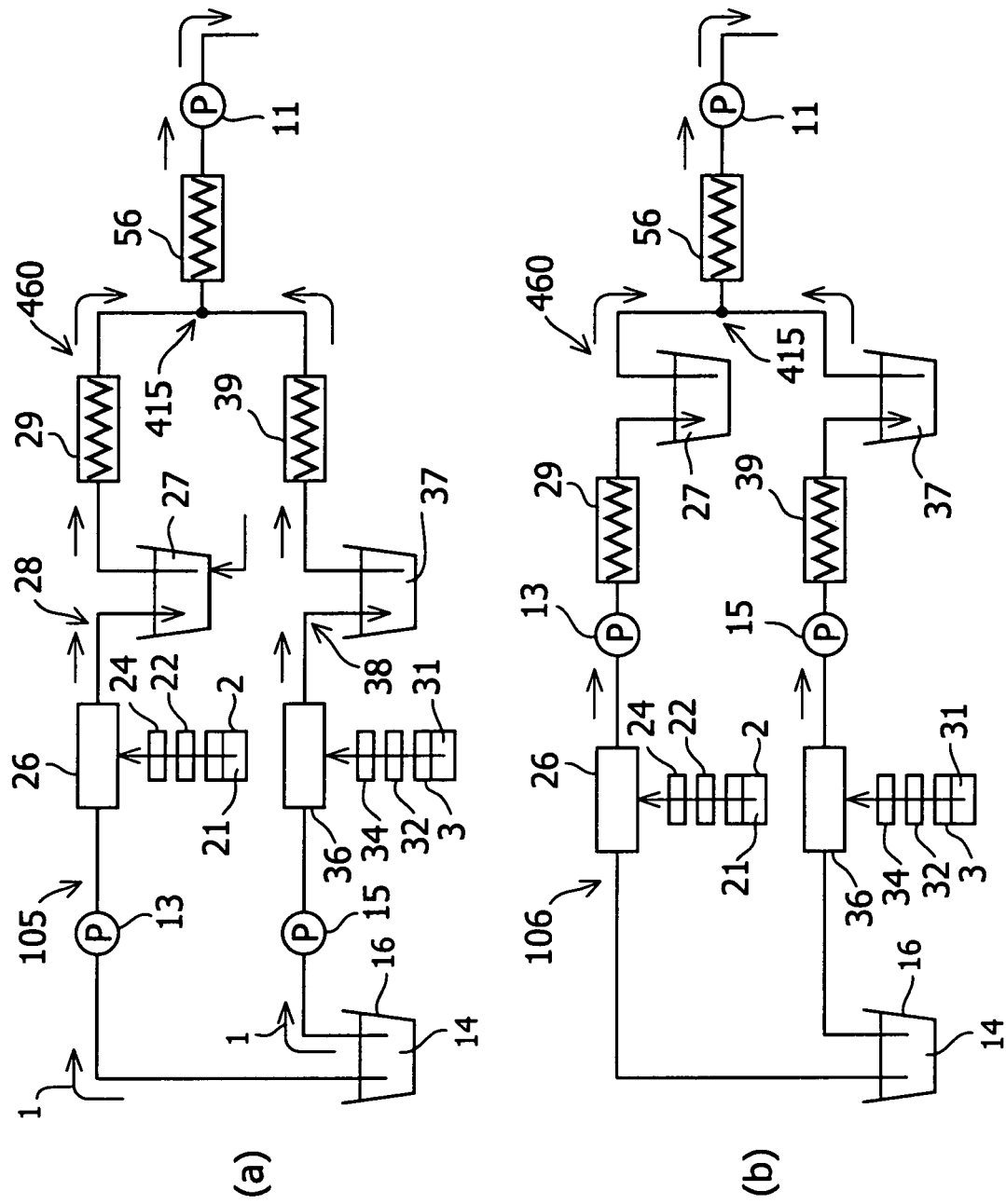
FIG. 16 is a system diagram showing a configuration of an apparatus for manufacturing sterilizing water in accordance with still another embodiment of the present invention.
Figure 17:
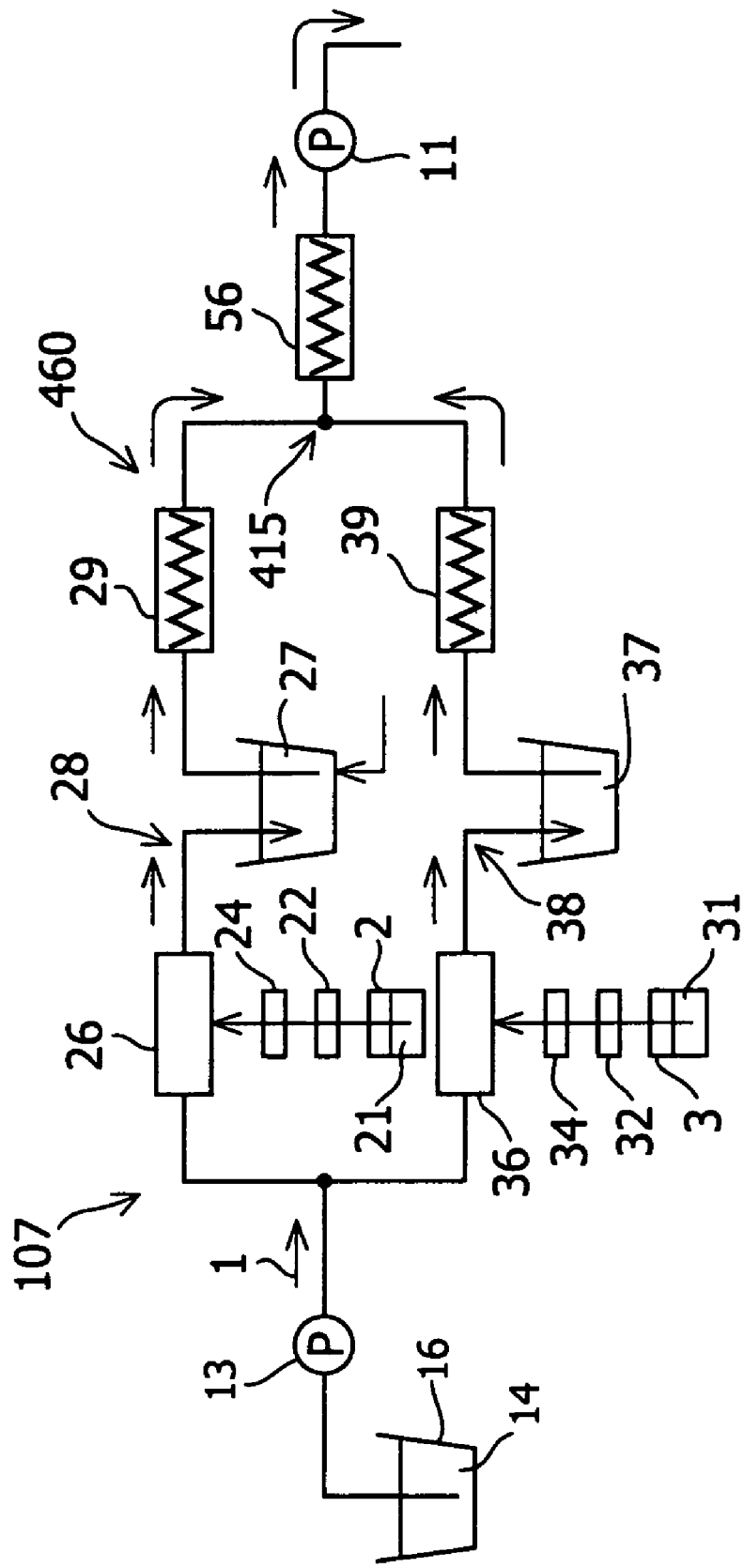
FIG. 17 is a system diagram showing a configuration of an apparatus for manufacturing sterilizing water in accordance with still another embodiment of the present invention.

Next, apparatuses 105, 106 and 107 for manufacturing sterilizing water having other configurations in this embodiment will be explained with reference to FIGS. 16 and 17. FIG. 16(a) shows the apparatus 105 for manufacturing sterilizing water, in which a raw water tank 16 is used in this embodiment, and a water flow to which the acid solution is fed and a water flow to which the chlorine-based solution is fed are supplied by using raw water pumps 13 and 15, respectively. If the apparatus for manufacturing sterilizing water is configured in this manner, the water flows to which the acid solution 21 and the c chlorine-based solution 31 are fed are controlled by the pumps 13 and 15, respectively. Thereby, in the case where the supply pressure of raw water fluctuates, for example, even if the raw water is, city water, the acid solution 21 and the chlorine-based solution 31 are fed stably, so that the manufacturing process of sterilizing water is stabilized. Also, as shown in the apparatus 106 for manufacturing sterilizing water shown in FIG. 16(b), the positions of the raw water pumps 13 and 15 may be on the downstream side of the feeders 26 and 36 for acid solution and chlorine-based solution. If a plurality of raw water pumps are used, a feeding operation matching the acid solution and chlorine-based solution can be performed. Further, as shown in the apparatus 107 for manufacturing sterilizing water shown in FIG. 17, only one raw water pump may be used before the raw water flow 1 is divided, not using the plural raw water pumps.

In this embodiment, an arrangement other than the arrangement of the acid solution mixer 29 and the chlorine-based solution mixer 39 shown in FIG. 8 can be used. Specifically, the acid solution mixer 29 can be provided between the acid solution feeder 26 and the dilute acid solution tank 27, and the chlorine-based solution mixer 39 can be provided between the chlorine-based solution feeder 36 and the dilute chlorine-based solution tank 37. For example, in the apparatus 105 for manufacturing sterilizing water shown in FIG. 16(a), the acid solution mixer 29 and the chlorine-based solution mixer 39 are arranged on the downstream side of the dilute acid solution tank 27 and the dilute chlorine-based solution tank 37, respectively, but in the apparatus 106 for manufacturing sterilizing water shown in FIG. 16(b), these mixers are arranged on the upstream side of the tanks.

For the acid solution 21, the feeding rate thereof to the water flow is controlled by a negative pressure produced by the water flow in the acid solution feeder 26 and restriction of flow rate due to a flow rate restricting orifice of the regulator 22. The feeding rate of the acid solution 21 is monitored by a flow sensor 24. The output of the flow sensor 24 is connected to a computer (not shown) to check whether or not the feeding rate is not higher than the upper limit value. For the chlorine-based solution as well, the feeding rate thereof is restricted by a regulator 32, and the feeding rate is monitored by a flow sensor 34. The chlorine-based solution is fed by being controlled by a negative pressure produced by the water flow in the chlorine-based solution feeder 36 and the regulator 32.

In the configuration shown in FIG. 8, since the dilute acid solution tank 27 and the dilute chlorine-based solution tank 37 store dilute solutions produced on the upstream side of these tanks, the pressure produced by the water flow on the upstream side is released once in these tanks. Therefore, the feeding rate of acid solution and the feeding rate of chlorine-based solution depend on the water pressure of the raw water 1. Also, the degrees of mixing in the acid solution mixer 29 and the chlorine-based solution mixer 39 depend on the water flow produced by the pump 11. Therefore, for example, even if the quantity of sterilizing water consumed is varied by the opening/closing of the faucet on the downstream side of the pump 11, the concentration of dilute acid solution and the concentration of dilute chlorine-based solution do not change due to the feeding of acid solution and the feeding of chlorine-based solution.

A suitable liquid level sensor, not shown, can be used for the dilute acid solution tank 27 and the dilute chlorine-based solution tank 37, and an electromagnetic valve etc. can be provided at a position between the division point of the raw water 1 and the acid solution feeder 26 and the chlorine-based solution feeder 36, by which the quantities of dilute acid solution and dilute chlorine-based solution can be controlled according to the position of liquid level sensor by suitable control. By this control, for example, a changeover between the state of flow rate capable of properly performing feeding and the state in which no water flow is present can be carried out. That is to say, the quantity of sterilizing water consumed through the faucet need not necessarily be reflected directly, and simple control of ON/OFF only can be carried out. This electromagnetic valve may further be restricted by the feeding rate detected by the flow sensors 24 and 34.

The raw water 1 is not subject to any special restriction, and pure water, city water, river water, underground water, and the like can be used according to the situation. As the acid solution 21, hydrochloric acid (hydrogen chloride solution) with a suitable concentration (for example, 8.5%), acetic acid, and the like are used. Also, as the chlorine-based solution 31, sodium hypochlorite solution with a suitable concentration (for example, 12%), chlorine dioxide, and the like are used.

Fifth Embodiment

Figure 9:
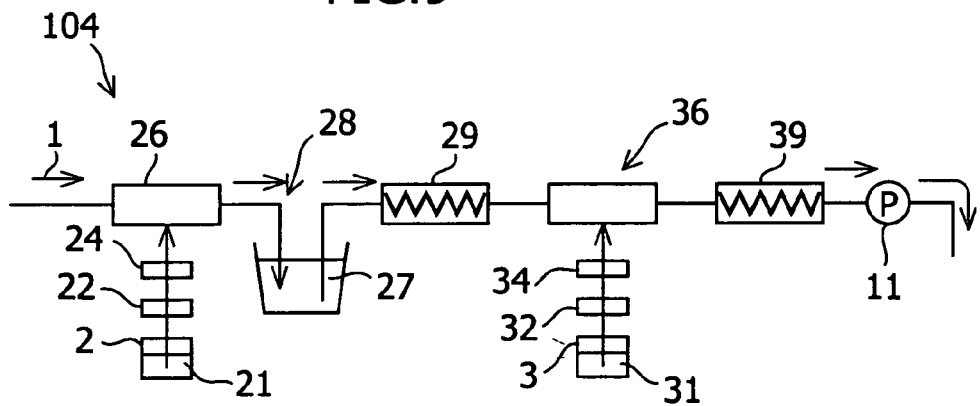
FIG. 9 is a system diagram showing a configuration of an apparatus for manufacturing sterilizing water in accordance with still another embodiment of the present invention.

Still another embodiment of the present invention will be explained. FIG. 9 is a system diagram showing a configuration of an apparatus 104 for manufacturing sterilizing water in accordance with one embodiment of the present invention. In FIG. 9, the same reference numerals are applied to the same elements as those in FIG. 8 etc.

In the apparatus 104 for manufacturing sterilizing water as well, the raw water 1 is supplied under pressure by suitable means. In this embodiment, the water flow of the raw water 1 is not divided. The acid 21 is fed from the acid solution tank 20 by the acid solution mixer 26 to yield the dilute acid solution, which is stored in the dilute acid solution tank 27. The dilute acid solution is sucked by the pump 11 to form a water flow. The chlorine-based solution 31 is fed to this water flow by the chlorine-based solution feeder 36, and the water flow is mixed homogeneously by the chlorine-based solution mixer 39, by which sterilizing water is manufactured. The faucet, not shown, etc. are provided on the downstream side of the pump 11, so that the sterilizing water is consumed through the faucet etc. The acid solution mixer 29 is arranged at any position in the water path between the acid solution feeder 26 and the chlorine-based solution feeder 36. In FIG. 9, it is arranged between the dilute acid solution 27 and the chlorine-based solution feeder 36.

In the configuration shown in FIG. 9, since the dilute acid solution tank 27 stores a dilute solution produced on the upstream side of the tank, the pressure produced by the water flow on the upstream side is released once in this tank. Therefore, the feeding rate of acid solution depends on the water flow (water pressure) of the raw water 1. Also, the water flow caused by suction accomplished by the pump 11 exerts an influence on the feeding rate of the chlorine-based solution 31 and the degrees of mixing in the acid solution mixer 29 and the chlorine-based solution mixer 39. Even if the quantity of sterilizing water consumed is varied by the opening/closing of the faucet on the downstream side of the pump 11, the concentration of dilute acid solution does not change due to the feeding of acid solution.

Figure 18:
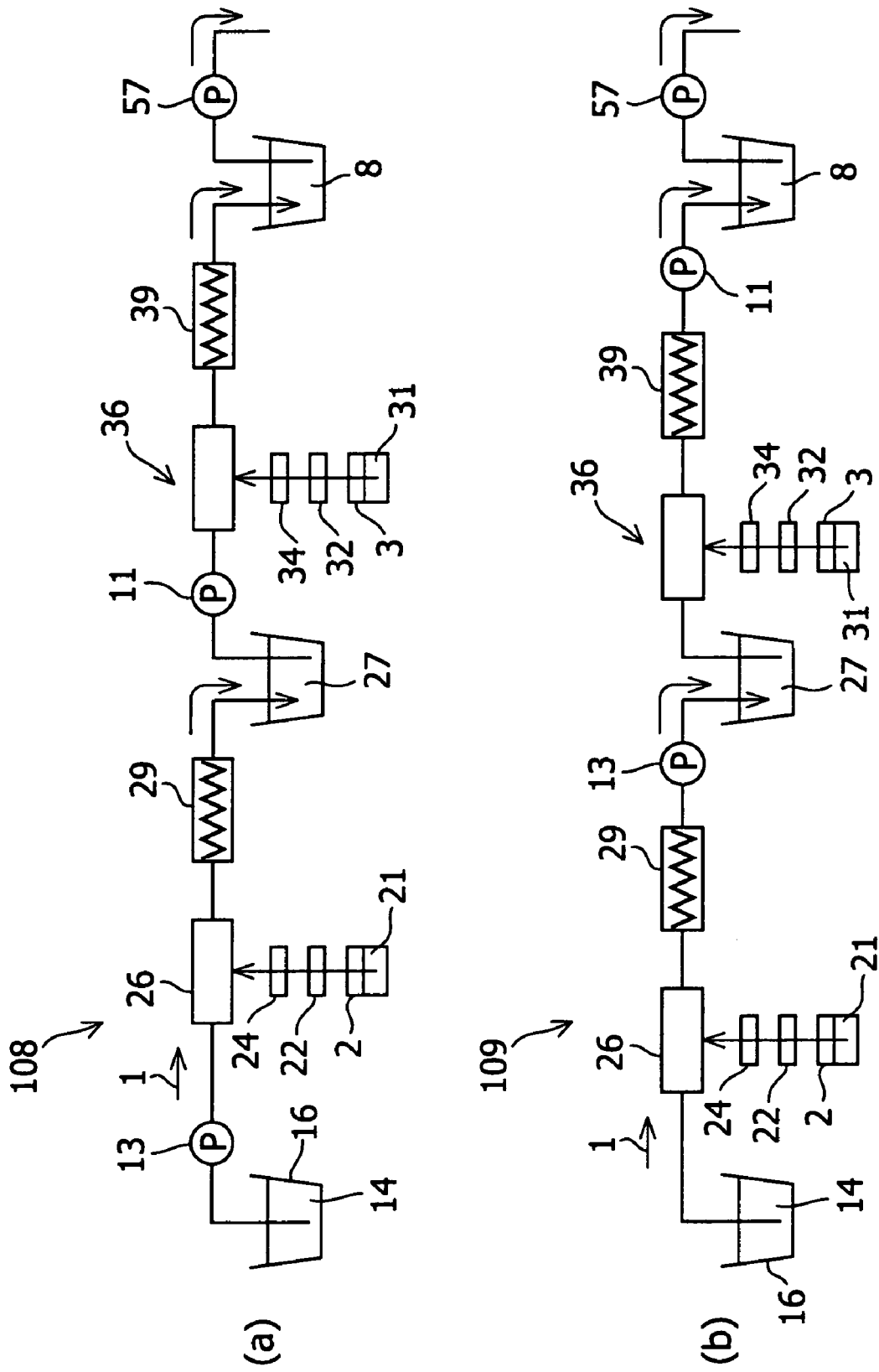
FIG. 18 is a system diagram showing a configuration of an apparatus for manufacturing sterilizing water in accordance with still another embodiment of the present invention.

Also, apparatuses 108 and 109 for manufacturing sterilizing water having other configurations of this embodiment are explained with reference to FIG. 18. These apparatuses 108 and 109 for manufacturing sterilizing water show examples in which the raw water tank 16 is used. In the apparatus 108 for manufacturing sterilizing water shown in FIG. 18(*a*), the raw water pump 13 sucks the raw water from the raw water tank 16 for forming a water flow, and the acid solution 21 is fed to this water flow. The dilute acid solution is stored in the dilute acid solution tank 27. Thus, the acid solution is fed to the water flow that is controlled by the raw water pump 13, so that even if the source of raw water is city water etc. (not shown), stable feeding of acid solution is realized. The manufactured sterilizing water is stored in the sterilizing water tank 8, and is taken out of the sterilizing water tank by a pump 57 as necessary. In the apparatus 109 for manufacturing sterilizing water shown in FIG. 18(*b*), the raw water pump 13 is arranged on the downstream side of the acid solution feeder 26. In this case as well, the same effects as those in the apparatus shown in FIG. 18(*a*) are achieved.

A suitable liquid level sensor etc. are used for the dilute acid solution tank 27, and an electromagnetic valve etc. are provided on the upstream side of the acid solution feeder 26, by which the quantity of dilute acid solution can be controlled by suitable control. The quantity of sterilizing water consumed through the faucet need not necessarily be reflected directly in this control. The regulators 22 and 32, the flow sensors 24 and 34, the electromagnetic valve, the control method thereof, and the like are the same as those in the fourth embodiment.

Sixth Embodiment

Figure 12:
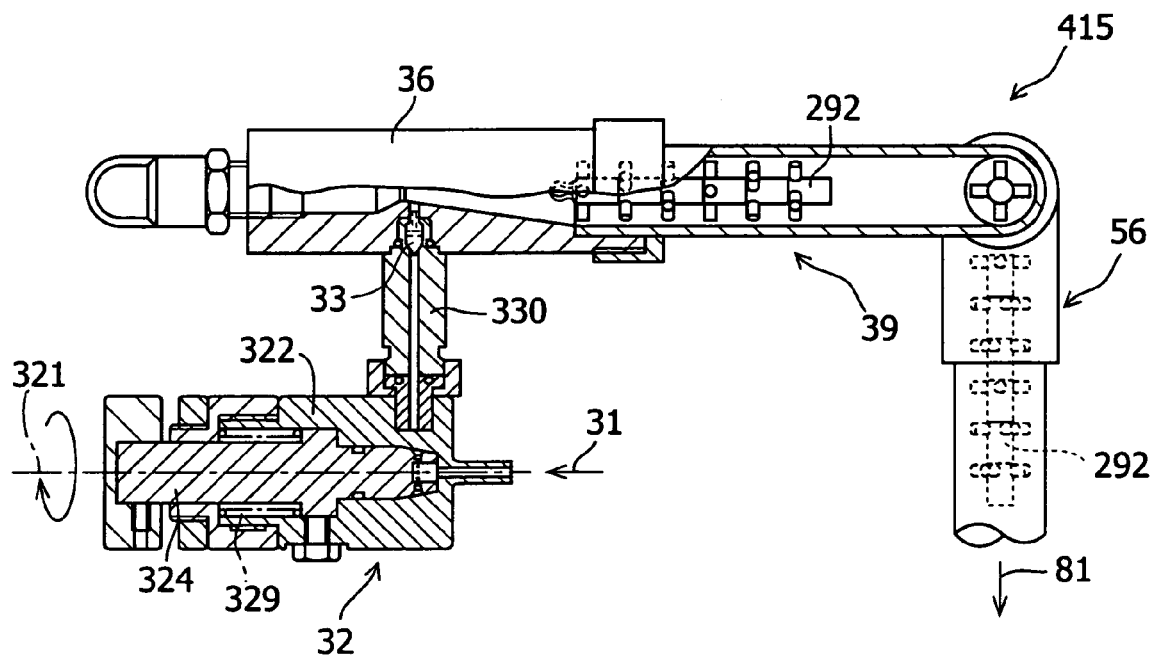
FIG. 12 is a partially sectional side view showing a construction of an assembly in accordance with an example of the present invention.
Figure 19:
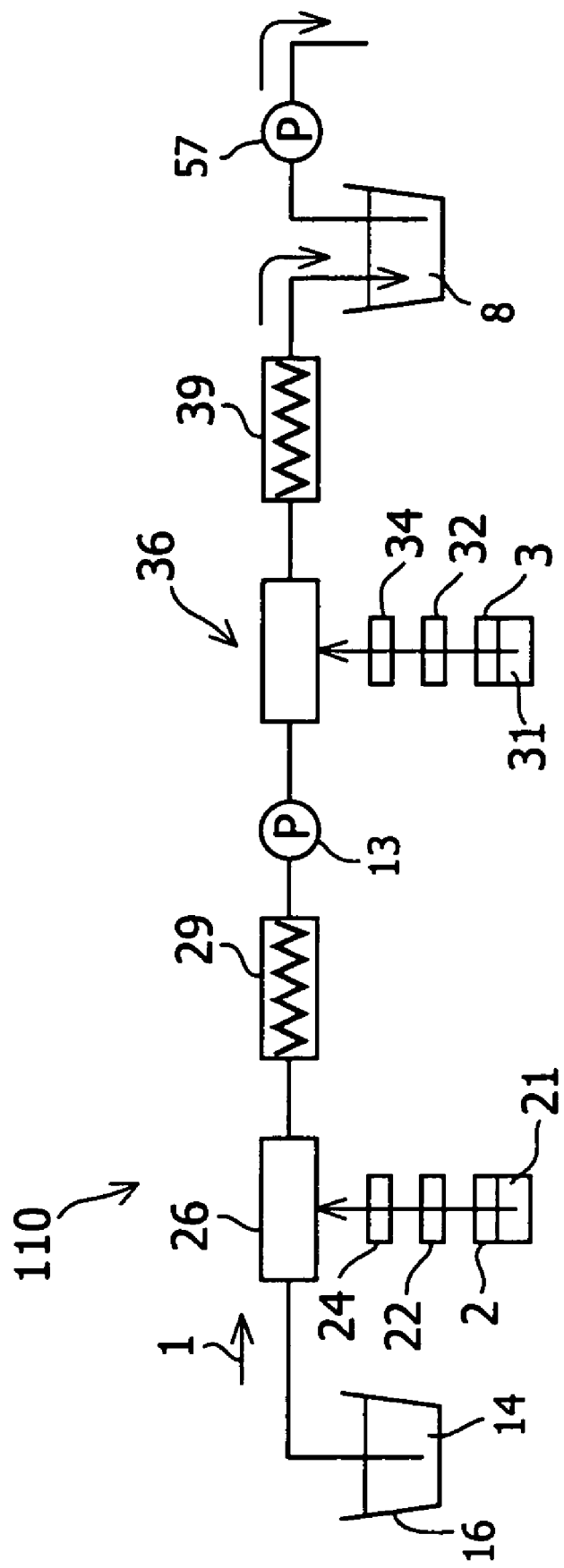
FIG. 19 is a system diagram showing a configuration of an apparatus for manufacturing sterilizing water in accordance with still another embodiment of the present invention.

An apparatus 110 for manufacturing sterilizing water in accordance with still another embodiment of the present invention will be explained with reference to FIG. 19. In this apparatus 110 for manufacturing sterilizing water, the dilute acid solution tank 27 is not used, and the raw water tank 16 is used. The position of the raw water pump 13 is not subject to any special restriction. The raw water pump 13 may be located just on the downstream side of the raw water tank, on the downstream side of the acid solution mixer 29 as shown in FIG. 12, or on the downstream side of the chlorine-based solution mixer 39. Without the use of the dilute acid solution tank 27, the use of the raw water tank realizes the stable feeding of acid solution and chlorine-based solution and hence enables stable manufacture of sterilizing water even if the raw water is city water etc. (not shown) whose pressure fluctuates. The sterilizing water thus manufactured is stored in the sterilizing water tank 8, and is consumed by being taken out by the pump 57 etc. as necessary.

Seventh Embodiment

Figure 10:
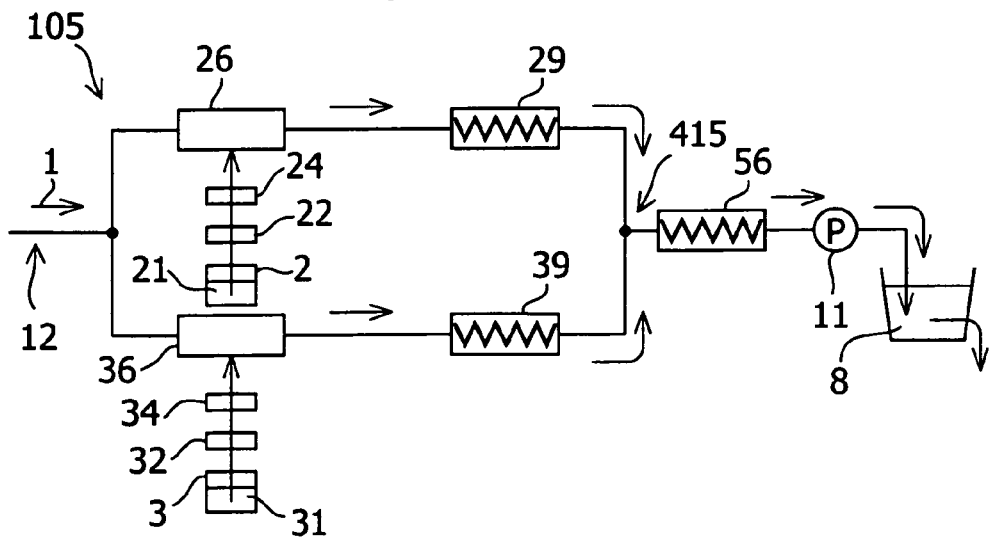
FIG. 10 is a system diagram showing a configuration of an apparatus for manufacturing sterilizing water in accordance with still another embodiment of the present invention.

Still another embodiment of the present invention will be explained. FIG. 10 is a system diagram showing a configuration of an apparatus 105 for manufacturing sterilizing water in accordance with one embodiment of the present invention. In this embodiment, the dilute acid solution tank 27 and the dilute chlorine-based solution tank 37 are removed from the apparatus 103 for manufacturing sterilizing water (FIG. 8), and the sterilizing water tank 8 is used after the manufacture of sterilizing water.

The advantages of the apparatus 105 for manufacturing sterilizing water over the apparatus 103 for manufacturing sterilizing water are as follows: the raw water 1 need not necessarily be supplied under pressure from the upstream side, and the manufacturing conditions are not affected by the usage of sterilizing water because the mixing situation after the feeding of acid solution and chlorine-based solution to the water flow or the dilution thereof for the manufacture of sterilizing water and the usage of sterilizing water are independent from each other.

In FIG. 10, a suitable liquid level sensor etc. is used for the sterilizing water tank 8, and an electromagnetic valve etc. is provided in front of the division point of path of the raw water 1, by which the quantity of dilute acid solution can be controlled by suitable control. The quantity of sterilizing water consumed through the faucet need not necessarily be reflected directly in this control. The regulators 22 and 32, the flow sensors 24 and 34, the electromagnetic valve, the control method thereof, and the like are the same as those in the fourth and fifth embodiments.

EXAMPLE

A more detailed example and a modification thereof of the apparatus 105 for manufacturing sterilizing water described in the seventh embodiment will now be described with reference to FIGS. 11 to 15.

Figure 11:
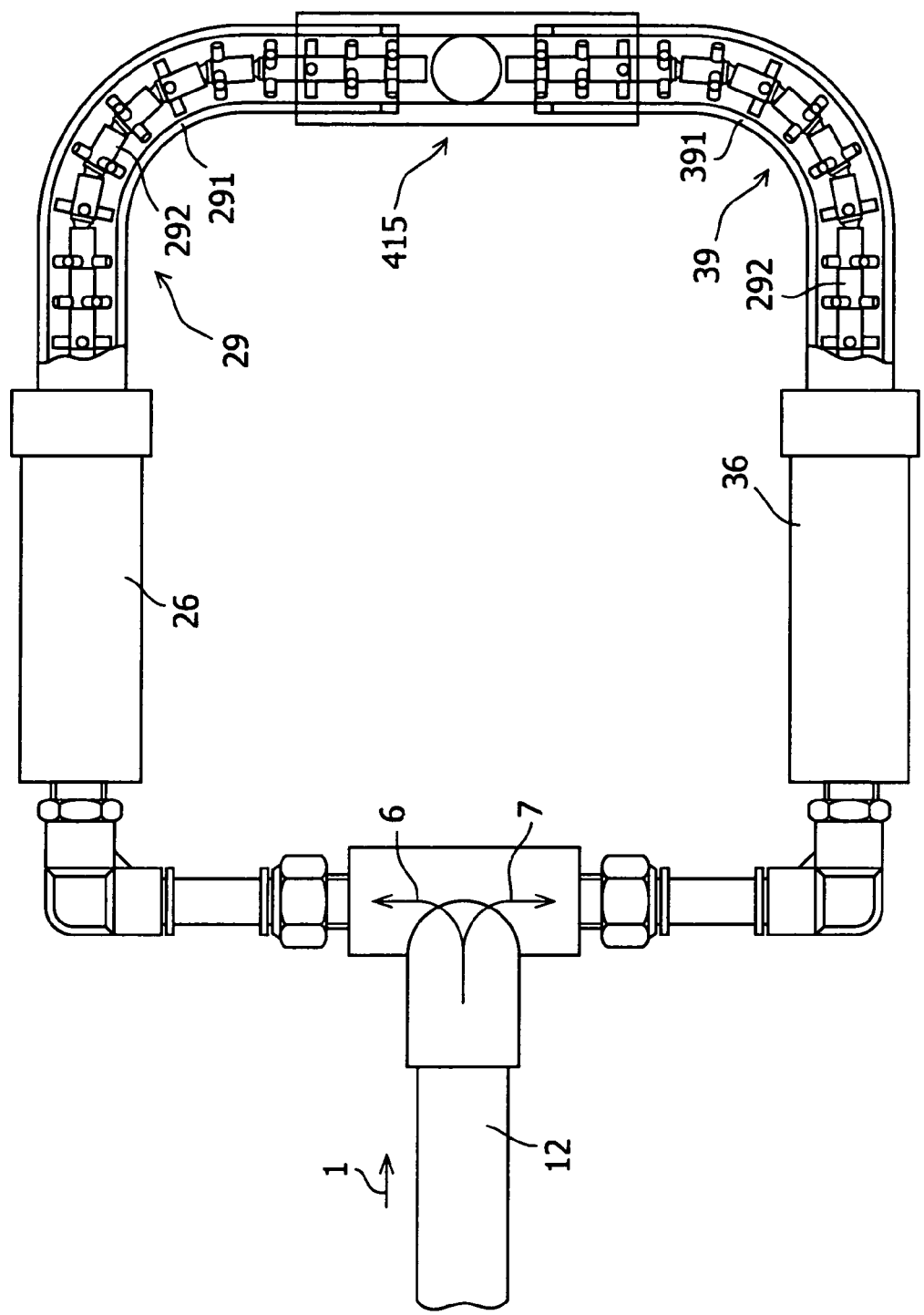
FIG. 11 is a partially sectional plan view showing a construction of an assembly in accordance with an example of the present invention.

FIG. 11 is a partially sectional plan view showing a construction of an assembly from the water path 12 to the joining mixer 56 in the example of the apparatus 105 for manufacturing sterilizing water. FIG. 12 is a partially sectional side view of the assembly shown in FIG. 11. According to the construction of this example, the chemicals (FIG. 12 shows only the chlorine-based solution 31) are fed to and mixed with the raw water 1, by which the sterilizing water 81 is manufactured.

The water path 12 is divided, and the water flows 6 and 7 enter the acid solution feeder 26 and the chlorine-based solution feeder 36, respectively. On the downstream side of the feeders, the acid solution mixer 29 and the chlorine-based solution mixer 39 are connected, and the water flows 6 and 7 join together in the joining portion 415. On the downstream side of the joining portion 415, the joining mixer 56 is connected.

The acid solution mixer 29 and the chlorine-based solution mixer 39 have tubes 291 and 391 each serving as a water path, respectively. In the tube, mixing elements 292 are provided so as to be in contact with the inside of the tube. The mixing elements 292 are arranged in a plural number in the direction of the axis of the tubes 291 and 391 for forming the water flow.

(Construction of Feeder)

As shown in a partial cross section in FIG. 12, the feeder is a feeder utilizing the flow velocity of water flow. The water flow is throttled once, and the chemical (in FIG. 12, the chlorine-based solution 31) of the quantity according to the water flow is fed to the water flow by a negative pressure produced by the water flow which has been throttled and increased in velocity. In this water path for feeding, a check valve 33 is provided. The check valve 33 prevents the raw water from flowing to the chemical side even if the pressure on the water flow side becomes higher than that on the chemical side for any reason.

(Construction of Mixing Element)

Figure 13:
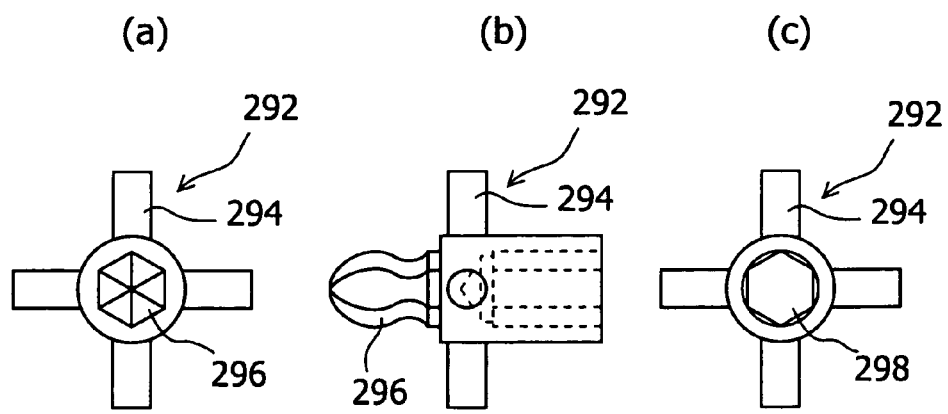
FIG. 13 is a view showing a construction of a mixing element used in an example of the present invention.

As shown in FIG. 13, each of the mixing elements 292 has a convex portion 296 and a concave portion 298 of a joint having a hexagonal cross section. The convex portion 296 and the concave portion 298 of the adjacent mixing elements are fitted to each other (FIGS. 11 and 12), and the angular difference around the axis is kept. Since the joint has a hexagonal cross section, in this example, the angular difference between the adjacent mixing elements is a multiple of 60 degrees.

The concave portion 298 of the joint has a shape of hexagonal prism. However, the convex portion 296 is not of a prismatic shape, though the cross section thereof is a hexagonal shape, and has a flexible construction such that the direction thereof can be changed freely to some extent so as to match the bend of the tubes 291 and 391 while being fitted to the concave portion 298. In this example, the convex portion 296 has a shape such as to be the tip end portion of a ball-pointed type hexagonal wrench. Thereby, even when the arrangement direction of the mixing elements 292 is bent along the bend of tube, the angular difference between the adjacent mixing elements is kept in the same way as the case where the tube is not bent. Although the joint of mixing element in this example is manufactured so as to have a hexagonal cross section, the joint may have a cross section of triangular, square, or the like shape. In particular, a regular polygon having an arbitrary number of sides is preferable.

The mixing element 292 has a block rod substantially protruding into the flow. In FIG. 13, this block rod 294 has a cross section of a circular shape. The block rod 294 has an operation for generating Karman vortexes, and hence generating a substantially turbulent flow in the flow in the tube. Although the block rod 294 can have a shape other than the circular cylinder, circular cylinder is favorable because it generates a turbulent flow efficiently and has low resistance.

In the mixing element 292 of this example, the block rod 294 protrudes in four directions, but it is not necessarily required to protrude in four directions. In order to achieve stronger mixing, a larger number of block rods can be used. Conversely, a smaller number of, for example, three block rods can be used. Since the block rod 294 protrudes in four directions and the joint has a hexagonal shape, if the adjacent mixing elements 292 are fitted to each other so as to shift by 60 degrees, the block rods of the adjacent mixing elements are also arranged so as to shift by 60 degrees. Thereby, as the flow in the tubes 291 and 391 passes through the plural mixing elements, the block rods 292 act on various portions of the flow, by which satisfactory mixing is realized. FIGS. 11 and 12 show the state in which the mixing elements 294 are arranged at various angles.

(Construction of Regulator)

Figure 14:
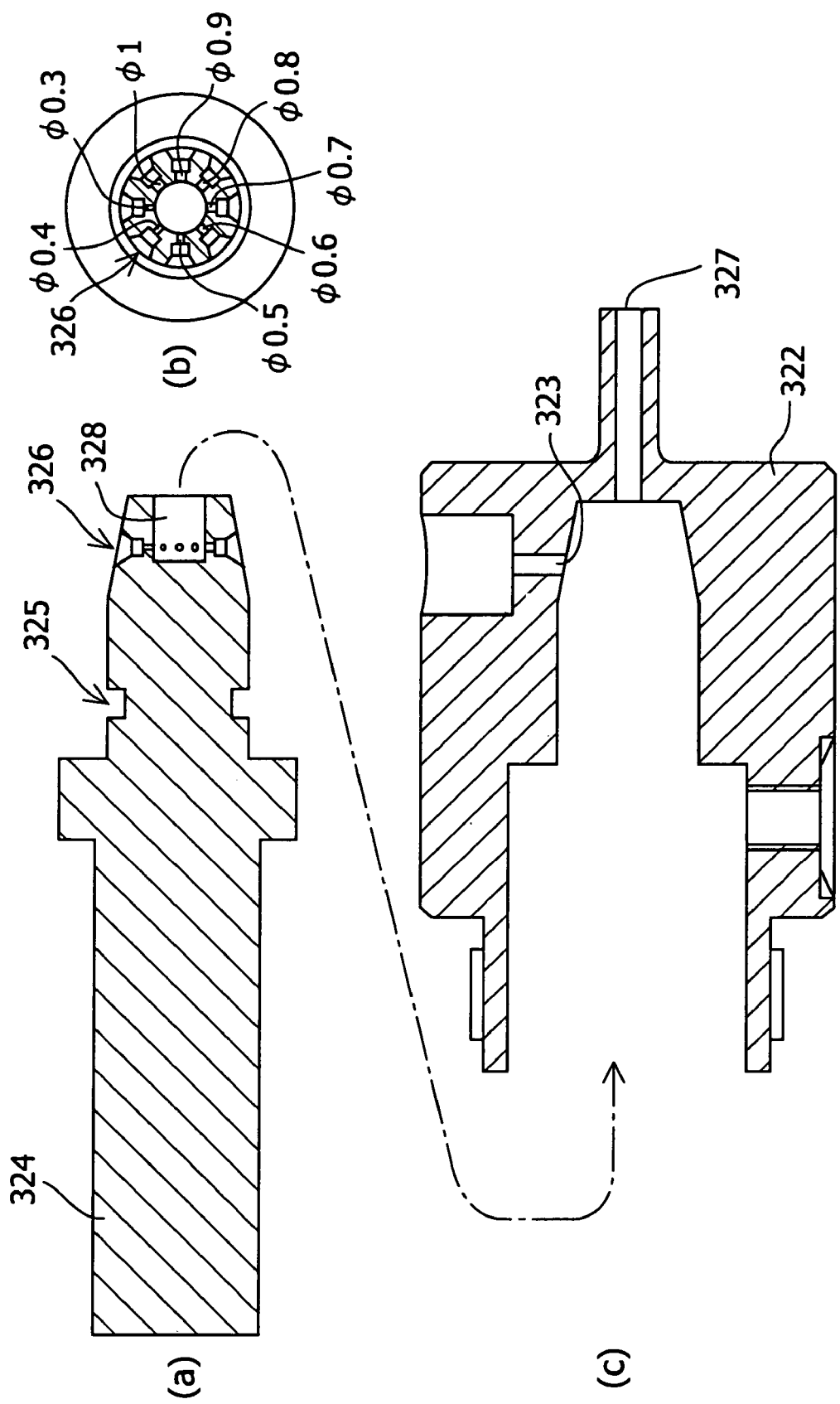
FIG. 14 is a sectional view showing a construction of a principal part of a regulator used in an example of the present invention.

Also, the regulator 32 (FIGS. 12 and 14) includes a turret portion 324, which is provided rotatable around the rotation center 321 and is provided with a plurality of flow rate restricting orifices 326 having different inside diameters (in FIG. 14(b), 0.3 to 1.0 mm in diameter), and a turret receiving portion 322, which has a flow path 323 aligning with any of the flow rate restricting orifices 326. The turret receiving portion 322 has a flow path 327 connected to the chlorine-based solution tank 30 (not shown in FIGS. 12 to 15). The chlorine-based solution flows into the regulator 32 through the flow path 327, entering a recess portion 328 in the turret portion, and flows out to the flow path 323 after passing through the orifice aligning with the flow path 323 of the flow rate restricting orifices.

An O-ring groove 325 is provided around the turret portion 324, and an O-ring (not shown) is fitted in the O-ring groove 325. In this state, the turret portion 324 is inserted into the turret receiving portion 322. The turret portion 324 is pressed against the turret receiving portion 322 by a spring 329 (FIG. 12) to maintain airtightness. However, the turret portion 324 can be turned around the rotation center 321 without a heavy burden imposed on the O-ring. By turning the turret portion 324, the flow rate restricting orifice used can be selected appropriately.

In FIG. 12, a flow path 330 is interposed between the regulator 32 and the chlorine-based solution feeder 36. In a modification of this example, in place of the flow path 330, the flow sensor 34 can be used. As the flow sensor 34, for example, a flow sensor shown in FIG. 15 can be used.

Figure 15:
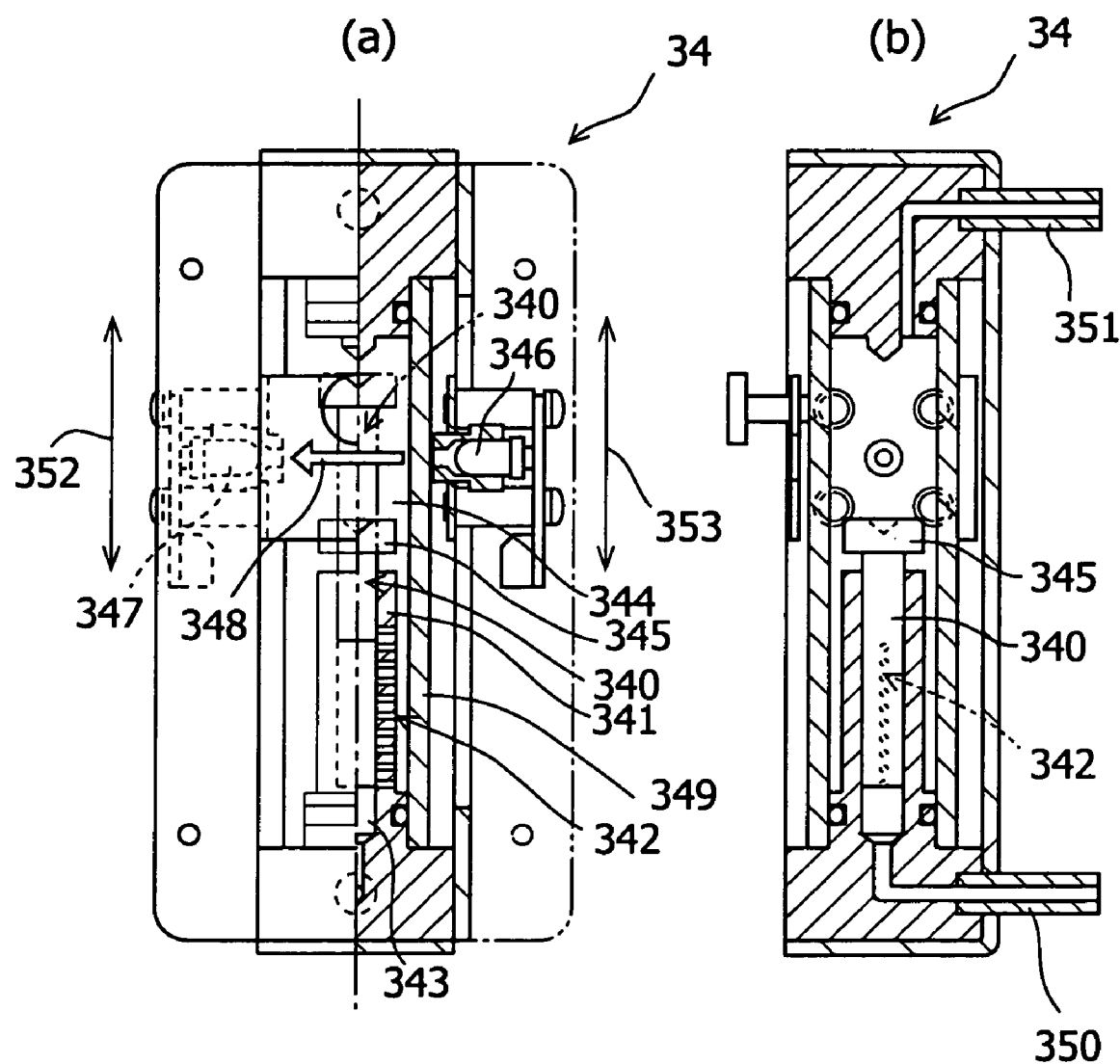
FIG. 15 is a sectional view showing a construction of a flow sensor used in an example of the present invention.

The flow sensor 34 shown in FIG. 15 is manufactured so that a cylindrical piston member 340, which is made of a material having light transmitting properties, can be moved vertically in the figure. A cylinder portion 341, which has a cylindrical inside side surface with an inside diameter slightly larger than the diameter of the cylindrical portion of the piston member, holds the piston member 340. The cylinder portion 341 is provided with a plurality of minute holes 342. The minute holes 342 are provided in one row as being arranged in a straight line form in the figure. However, the minute holes 342 may be arranged in other ways.

The cylinder portion 341 and the piston member 340 separate a front chamber 343 from the rear chamber 344. However, the front chamber 343 and the rear chamber 344 are connected to each other by the plural minute holes 342.

The piston member 340 is provided with a light intercepting member 345, which moves along with the movement of the piston member 340.

A light emitting element 346 is a light emitting element that emits a suitable light, such as a red light emitting diode, and is arranged so that the emitted light forms a light path 348 in the range in which the light intercepting member 345 moves together with the piston member 340.

A light receiving element 347 is provided so as to receive the light of the light emitting element 348, and is arranged so as to be capable of detecting that the light intercepting member 345 intercepts the light path 348.

The rear chamber 344 is covered with an external cylinder member 349 having light transmitting properties, so that the detection of position of the light intercepting member 345 due to light is not hindered.

This flow sensor 34 is used in an orientation such that when a movable member moves downward due to the gravity, the minute holes 342 are closed.

The movable member consisting of the light intercepting member 345 and the piston member 340 closes at least some minute holes 342 if a differential pressure obtained by subtracting the pressure of a working fluid in the rear chamber 344 from the pressure of a working fluid in the front chamber 343 is not higher than a predetermined pressure (working pressure). Depending on the arrangement of the minute holes 342, all or only some of the minute holes 342 may be closed.

The working pressure by which the movable member is moved is defined as a difference in pressure (differential pressure) between the pressure in the front chamber 343 and the pressure in the rear chamber 344, for example, such as to give an upward force that is the same as a downward force obtained by removing a buoyancy exerted on the movable member by the working fluid from the gravity due to the mass of the movable member. In this example, preferably, the materials of the piston member 340 and the light intercepting member 345 are selected so that the downward force remains according to the gravity even if the buoyancy of the working fluid acts, that is, the movable member has a greater specific gravity than the working fluid.

Also, if the differential pressure becomes higher than the working fluid, the moving member is displaced upward according to the differential pressure, and operates so that the closed minute holes 342 are opened in succession, and thereby a larger quantity of working fluid is caused to flow from the front chamber to the rear chamber. Since the minute holes connect the front chamber 343 to the rear chamber 344, if more minute holes are opened, the working fluid flows through the minute holes so as to eliminate the differential pressure. Thereby, the conductance of fluid between the front chamber 343 and the rear chamber 344 is increased, and varies in the direction such that the differential pressure is eliminated. For example, if the differential pressure becomes equal to the working pressure that causes the movement of movable member, the movable member does not move further. Thus, the flow sensor 34 of this example can detect the flow rate of working fluid via the displacement of movable member caused by the differential pressure.

When the light intercepting portion 345 of the movable member that is displaced by a change in differential pressure intercepts the light path 348, the quantity of detected light received by the light receiving element is changed thereby, and this change is output as an output signal. This output signal is input in, for example, a computer (not shown), and is monitored. Thereby, for example, if the feeding rate of chlorine-based solution exceeds a predetermined value, an electromagnetic valve (not shown) provided at a suitable position is controlled accordingly, and thereby the manufacture of sterilizing water can be stopped.

It is a matter of course that the sensitivity and application range of flow sensor can be set suitably by appropriately adjusting the arrangement and sizes of the minute holes 342 or by appropriately adjusting the positions of the light emitting element 346 and the light receiving element 347 as indicated by arrow marks 352 and 353 in FIG. 15. Also, in FIG. 15(b), an inlet 350 and an outlet 351 of the flow sensor 34 are provided at the side of the flow sensor 34. However, the configuration can be such that the inlet 350 is provided in the bottom surface and the outlet 351 is provided in the top surface to match the flow path 330 (FIG. 12). Also, although explanation has been given of the feeding and mixing of the chlorine-based solution, for the feeding and mixing of acid solution as well, the same feeder, regulator, flow sensor, and the like can be used.

Eighth Embodiment

Figure 20:
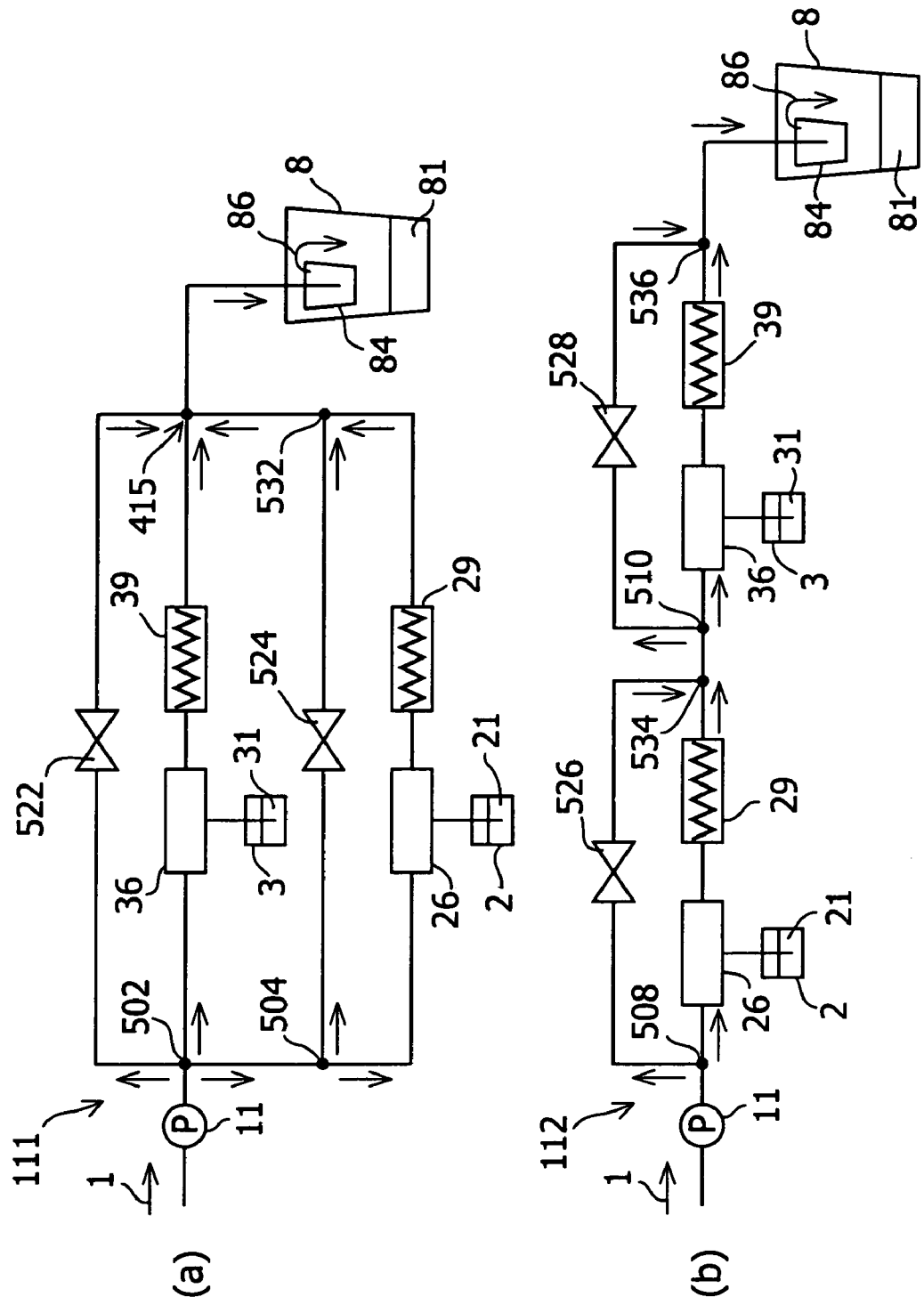
FIG. 20 is a system diagram showing a configuration of an apparatus for manufacturing sterilizing water in accordance with still another embodiment of the present invention.

FIG. 20 is a system diagram for illustrating still another embodiment of the present invention, in which bypass water paths are used. In this embodiment, the bypass water path is used for each feeder. Thereby, the concentration can be regulated to some extent even in the case where a feeder that does not have a regulating mechanism for the feeding rate of acid solution or chlorine-based solution is used.

FIG. 20(a) shows an apparatus 111 for manufacturing sterilizing water, which realizes the water flow to which acid solution is fed and the water flow to which chlorine-based solution is fed by separate water paths (first and second water paths).

The apparatus 111 for manufacturing sterilizing water includes the pump 11, dividing portions 502 and 504, the acid solution feeder 26 (first feeder), the acid solution mixer 29, and a water path (first water path) reaching the sterilizing water tank 8 through a joining portion 532 and the joining portion 415.

Also, the apparatus 111 for manufacturing sterilizing water has a water path (second water path) which has the chlorine-based solution feeder 36 (second feeder) and the chlorine-based solution mixer 39 in the path, and divides from the first water path in the dividing portion 502 on the upstream side of the acid solution feeder 26 and joins again to the first water path in the joining portion 415 on the downstream side of the acid solution feeder 26.

Further, the apparatus 111 for manufacturing sterilizing water has, in addition to the first and second water paths, a first bypass water path which has a flow rate restricting valve 524 in the path, and bypasses the first feeder by dividing from the first water path in the dividing portion 504 on the upstream side of the acid solution feeder 26 (first feeder) and by joining again to the first water path in the joining portion 532 on the downstream side of the acid solution feeder 26.

In addition, the apparatus 111 for manufacturing sterilizing water has a second bypass water path which has a flow rate restricting valve 522 in the path, and bypasses the second feeder by dividing from the second water path in the dividing portion 502 on the upstream side of the chlorine-based solution feeder and by joining again to the second water path in the joining portion 415.

The flow rate restricting valve 524 has a function for mainly regulating the raw water that further dilutes the dilute acid solution having been diluted by the feeding of acid solution. Also, the flow rate restricting valve 522 has a function for mainly regulating the dilution of chlorine-based solution.

On the other hand, FIG. 20(b) shows an apparatus 112 for manufacturing sterilizing water, which realizes the water flow to which acid solution is fed and the water flow to which chlorine-based solution is fed by a series of water path (main water path).

The apparatus 112 for manufacturing sterilizing water has the pump 11, a dividing portion 508, the acid solution feeder 26 (first feeder), the acid solution mixer 29, a joining portion 534, a dividing portion 510, the chlorine-based solution feeder 36 (second feeder), the chlorine-based solution mixer 39, and a water path (main water path) reaching the sterilizing water tank 8 through a joining portion 536. The main water path is configured so that the raw water is introduced and the acidic water is fed, then the chlorine-based solution is fed, and the dilute solution having been mixed is caused to flow into the sterilizing water tank.

Also, the apparatus 112 for manufacturing sterilizing water has a first bypass water path which has a flow rate restricting valve 526 in the path, and bypasses the acid solution feeder 26 by dividing from the main water path in the dividing portion 508 on the upstream side of the acid solution feeder 26 and by joining again to the main water path in the joining portion 534 on the downstream side of the acid solution feeder 26 and on the upstream side of the chlorine-based solution feeder 36.

Further, the apparatus 112 for manufacturing sterilizing water has a second bypass water path which has a flow rate restricting valve 528 in the path, and bypasses the chlorine-based solution feeder 36 by dividing from the main water path in the dividing portion 510 on the downstream side of the joining portion 534 and on the upstream side of the chlorine-based solution feeder 36 and by joining again to the main water path in the joining portion 536 on the downstream side of the chlorine-based solution feeder 36.

The flow rate restricting valve 526 has a function for regulating the flow rate of raw water in the first bypass water path, which further dilutes the dilute acid solution having been diluted by the feeding of acid solution. Also, the flow rate restricting valve 528 has a function for regulating the flow rate in the second bypass water path through which dilute acid solution that need not be caused to flow in the chlorine-based solution feeder 36.

This embodiment, in both of the apparatuses for manufacturing sterilizing water, aims at realizing stable feeding while the flow rates of the acid solution and chlorine-based solution are restricted, restricting the tank volumes of the acid solution tank 2 and the chlorine-based solution tank 3 by increasing the concentration of the acid solution and chlorine-based solution, or increasing the sterilizing water capable of being manufactured with the same tank volume.

In the configurations of the apparatuses 111 and 112 for manufacturing sterilizing water, each of the feeders is a suction type feeder. In the path for the fed liquid, an electromagnetic valve etc. can be provided as necessary to carry out simple opening/closing control, but there is provided no mechanism for regulating the flow rate of the fed liquid.

For the suction type feeder, it is generally difficult to realize stable feeding at a feeding rate lower than a fixed rate. Also, the feeder of this type has a property that if the flow rate (or flow velocity) of water flow increases, the suction pressure of the acid solution or chlorine-based solution increases in accordance with Bernoulli theorem, and the feeding rate also increases. The feeder in accordance with this embodiment also has this property. For example, when the chemical is fed at a feeding rate not lower than 60 ml/min, preferably, at a feeding rate not lower than 80 ml/min, the acid solution feeder 29 and chlorine-based solution feeder 39 realize stable feeding. However, if the feeding rate is lower than the above-described value, stable feeding cannot be realized. Also, for the acid solution feeder 29 and chlorine-based solution feeder 39, the flow rate of water flow must be not lower than a fixed value to realize the above-described stable feeding. For example, for a certain feeder, when the flow rate is not lower than 7 liter/min, the feeding rate of chemical is 80 ml/min, so that the stable feeding is realized. Hereunder, for convenience of explanation, all feeders are assumed to be feeders of the same type as the above-described feeder. Also, in this embodiment, since it is desirable to make the flow rate low to restrain the consumption of the acid solution and chlorine-based solution, the operation in the case where the feeding rate is fixed (for example, 80 ml/min) is explained. In this case, the water flow (water flow in the first and second water path and the main water path) is fixed (for example, 7 liter/min) as a necessary consequence.

First, the case where sterilizing water of a quantity as small as possible is manufactured is considered. For this purpose, in any of the apparatuses for manufacturing sterilizing water, all flow rate restricting valves in the bypass water path are fully closed. In this case, in the configuration of the apparatus 111 for manufacturing sterilizing water, the raw water of the sum of the minimum flow rates for the first and second water paths has only to be supplied by the pump 11, and in the configuration of the apparatus 112 for manufacturing sterilizing water, the raw water of the minimum flow rate for the main water path has only to be supplied by the pump 11.

Therefore, in order to yield a small quantity of sterilizing water under a condition that the pump can regulate the flow rate freely and the same feeder is used, the configuration of the apparatus 112 for manufacturing sterilizing water is more suitable than that of the apparatus 111 for manufacturing sterilizing water. Also, in the case where the intended yielding quantity is larger than the yielding quantity of the apparatus 112 for manufacturing sterilizing water, the regulation of dilution accomplished by opening the flow rate restricting valve is easier in the apparatus 112 for manufacturing sterilizing water than in the apparatus 111 for manufacturing sterilizing water.

Next, the case where sterilizing water of a quantity as large as possible is manufactured is considered. In this case, the configuration is made such that the bypass water path has low resistance. Thereby, if the flow rate restricting valve in the bypass water path is opened sufficiently, a large quantity of the raw water 1 can be caused to flow even if the flow rate in the feeder is still kept at the minimum rate. In this case as well, a large quantity of sterilizing water can be manufactured by increasing the concentrations of acid solution and chlorine-based solution without changing the components of sterilizing water. Actually, there occurs a phenomenon that if the concentration of chlorine-based solution is too high, the sterilizing performance decreases earlier (deactivation). Therefore, the concentration of chlorine-based solution cannot be set freely, and also the pump has a limitation, which imposes a restriction. However, by changing the design appropriately based on the configuration of the apparatus for manufacturing sterilizing water in accordance with this embodiment, a large quantity of sterilizing water can be manufactured with small quantities of acid solution and chlorine-based solution.

For convenience of explanation, explanation has been given assuming that the feeding rates of acid solution and chlorine-based solution and the quantity of water in the feeder are fixed. Actually, however, a change in feeding rates of acid solution and chlorine-based solution increasing with the flow rate is considered, the flow rates in the first and second water paths and the main water path is kept as low as possible in the range in which the flow rates are higher than the lower limit value for realizing the stable feeding, and the valves in the bypass water paths are regulated so that the other flow rates are caused to flow in the bypass water path. Also, since the actual pump has a functional relation between pressure and water quantity, regulation closer to the actual situation can be accomplished by considering this fact.

In this embodiment, by the above-described configuration, the feeder can be operated under a condition suitable for the feeding, and the concentration of acid solution and chlorine-based solution can be decreased by using the downstream bypass water path. Therefore, the operations of feeding and dilution can be set so as to meet the respective objectives, so that the stable operation can be performed.

Furthermore, other features of this embodiment are explained. In the apparatuses 111 and 112 for manufacturing sterilizing water, a vessel 84 is used in the sterilizing water tank 8. This vessel 84 is a bucket-shaped vessel whose upper side is open, and is configured so as to once receive the sterilizing water 81 to be stored in the sterilizing water tank 8 and causes the sterilizing water to overflow the vessel (arrow mark 86 in FIG. 20). The water path for causing sterilizing water or raw water to flow into the sterilizing water tank has its outflow port disposed at an inside position lower than the top surface of the vessel 84 having a height 88 of water level at the overflow time (overflow level). Therefore, the pressure applied to the outflow port of water path (pressure due to water depth of sterilizing water) is fixed regardless of the quantity of sterilizing water stored in the sterilizing water tank. Thereby, the pressure applied to the outflow port is scarcely changed unless the distance from the overflow surface to the outflow port changes, so that a change in water pressure does not occur regardless of the quantity of sterilizing water in the sterilizing water tank 8. Therefore, the pressure on the downstream side of the suction type feeder is stabilized, and hence the feeding operation in the suction type feeder is stabilized.

Further, according to this configuration, no air intrudes from the outflow port of water path even when the apparatus is shut down.

In the above-described apparatuses 111 and 112 for manufacturing sterilizing water, even if the raw water has different acidities (pH), the pH of dilute acidic water at the intermediate stage (for example, the pH at the outlet of the acid solution mixer 29) can be made fixed by adjusting the flow rate restricting valve. Therefore, in the case where pH changes as actually found as a difference in water quality of city water between regions, the apparatus for manufacturing sterilizing water can be adjusted so as to match the difference in water quality by adjusting the flow rate restricting valve when the apparatus for manufacturing sterilizing water in accordance with this embodiment is installed. Also, unlike the apparatuses 111 and 112 for manufacturing sterilizing water, even in the case where the raw water is supplied by city water without the use of the pump 11, the manufacturing conditions for sterilizing water can be adjusted in accordance with the supply condition of raw water by adjusting the flow rate restricting valve in accordance with various supply quantities and water pressures.

[Effects of the Invention]

According to the above disclosure, in the present invention, in the apparatus for manufacturing sterilizing water, in which sterilizing water is manufactured by mixing a chlorine-based compound consisting of sodium hypochlorite or chlorine dioxide or a combination thereof and an acid solution consisting of hydrochloric acid etc. with water, the aqueous solution of chlorine-based compound can be made weakly acidic to neutral condition without the production or dissolution of chlorine gas. The feeder in accordance with the present invention can feed the acid solution and chlorine-based compound by a small and simple construction because it feeds both of the acid solution and the chlorine-based compound, and also realizes stable feeding.

Also, by the feeder using vortexes or a turbulent flow, which is used in the apparatus for manufacturing sterilizing water in accordance with the present invention, the concentration of sterilizing water is made uniform. Thereby, the chlorine concentration in the sterilizing water is made fixed, so that stable sterilization power is achieved. According to the configuration in accordance with the present invention in which the acid solution and chlorine-based compound are fed by suction utilizing a negative pressure produced in the water flow without the use of a pump, there is no pulsation at the time of feeding, and the concentrations of acid and chlorine in the water flow do not change with time. In addition, according to the configuration in which the pH of sterilizing water of the present invention is in the range of 4.8 to 7.5, the sterilization power is enhanced, and hence high sterilization power can be obtained by a lower concentration of chlorine-based solution.

According to the above disclosure, in the present invention, in the apparatus for manufacturing sterilizing water, in which sterilizing water is manufactured by feeding a chlorine-based compound consisting of sodium hypochlorite or chlorine dioxide or a combination thereof and an acid consisting of hydrochloric acid to water, the aqueous solution of chlorine-based compound can be made weakly acidic to neutral condition without the production or dissolution of chlorine gas. In the apparatus for manufacturing sterilizing water in accordance with the present invention, since a tank for appropriately releasing a pressure is used, the influence exerted on the manufacturing conditions by the usage situation of sterilizing water can be decreased, and hence sterilizing water having stable quality can be manufactured.

In the present invention, the chemical can be fed according to the water flow by using the water flow itself, or a static mixer can be used, so that the sterilizing water can be manufactured by a simple apparatus. Also, by using the raw water tank or the raw water pump, the water flow can be stabilized, so that the chemical can be fed more stably.

Also, by using the mixing elements of one shape, the flow at various positions in the tube can be made turbulent, and hence the mixing elements can be used at a place where the tube is bent.

Further, since a regulator that performs stable flow rate restricting operation can be realized, the flow rate can be controlled properly even in the case where the acidic water and chlorine-based solution with high concentration are fed to water little by little.

In addition, since even a minute flow can be detected stably, even at the time of manufacture of sterilizing water, the feeding rates of the acidic water and chlorine-based solution can be detected to appropriately shut down the apparatus, so that the sterilizing water can be manufactured safely.

If the bypass water path arranged in parallel with the feeder is used, and the flow rate restricting valve is further provided in the bypass water path, the flow rate in the bypass water path can be adjusted by fully opening, partially opening, or fully closing the valve. By adjusting the flow rate in the bypass water path at the time when the apparatus for manufacturing sterilizing water is installed, the manufacturing conditions for the sterilizing water can be kept proper even if the raw water for producing the sterilizing water has various supply quantities or pressures.

If the vessel for overflow is provided in the sterilizing water tank, the pressure on the downstream side of the suction type feeder provided in the water path is stabilized, so that the feeding operation of the suction type feeder is stabilized.

The invention claimed is:

1. An apparatus for manufacturing sterilizing water, in which sterilizing water is manufactured by mixing an acid solution consisting of hydrochloric acid or acetic acid or a mixture thereof and a chlorine-based solution consisting of sodium hypochlorite or chlorine dioxide or a mixture thereof with water, comprising:
   a feeder provided with a first flow path, in which the acid solution is fed to a part of a water flow to produce a dilute acid solution, and a second flow path, in which the chlorine-based solution is fed to a remainder of the water flow to produce a dilute chlorine-based solution, the feeder feeding the acid solution and the chlorine-based solution by suction utilizing a negative pressure produced in water flowing in the first and second flow paths, absent a pump;
   a mixer comprising a plurality of mixing blades, the mixer being arranged on the downstream side of the first and second flow paths to mix the dilute acid solution sent through the first flow path with the dilute chlorine-based solution sent through the second flow path; and
   a separation wall including a planar member extending along a longitudinal axis of the first and second flow paths that is configured to separate the first and second flow paths, wherein a downstream end portion of the separation wall is connected to the plurality of mixing blades.

2. The apparatus for manufacturing sterilizing water according to claim 1, characterized in that the feeder is provided with a movable portion that performs opening/closing operation of flow path for the water flow by the water supply pressure of water flow, and by the opening/closing operation, a check valve for feeding at least either of the acid solution and the chlorine-based solution is opened or closed.

3. The apparatus for manufacturing sterilizing water according to claim 1, characterized in that the mixer is a static mixer in which the water flow is mixed so as to be a substantially turbulent flow.

4. The apparatus for manufacturing sterilizing water according to claim 3, characterized in that the mixer is a mixer in which mixing is performed in the water flow in a tube, and is a static mixer in which the plurality of mixing blades having different directions are arranged in the tube along the lengthwise direction of the tube, and a substantially turbulent flow is produced in the water flow in the tube by each of the mixing blades, by which the water flow is mixed.

5. The apparatus for manufacturing sterilizing water according to claim 4, characterized in that the mixing blades are manufactured by twisting a flat plane shaped plate member in connecting portions with narrow widths, which are provided on the plate member.

6. The apparatus for manufacturing sterilizing water according to claim 1, characterized in that the water flow is produced by a pump located on the upstream side of the feeder.

7. The apparatus for manufacturing sterilizing water according to claim 1, wherein the feeder is configured to divide an input flow path into the first and second flow paths.

8. The apparatus for manufacturing sterilizing water according to claim 1, further comprising an acid tank configured to feed an acid to water in the first flow path and a chlorine-based solution tank configured to feed a chlorine-based solution to water in the second flow path.

9. The apparatus for manufacturing sterilizing water according to claim 8, wherein the acid tank comprises an acid solution and the chlorine-based tank comprises a chlorine-based solution.

10. The apparatus for manufacturing sterilizing water according to claim 9, characterized in that the chlorine-based solution is sodium hypochlorite, and the pH of the sterilizing water is in the range of 4.8 to 7.5.

11. The apparatus for manufacturing sterilizing water according to claim 1, wherein the planar separation wall extends along a longitudinal axis of the feeder.

* * * * *